US009315560B2

(12) United States Patent
Mitterer et al.

(10) Patent No.: US 9,315,560 B2
(45) Date of Patent: Apr. 19, 2016

(54) PURIFICATION OF VWF FOR INCREASED REMOVAL OF NON-LIPID ENVELOPED VIRUSES

(75) Inventors: Artur Mitterer, Orth/Donau (AT); Meinhard Hasslacher, Vienna (AT); Christa Mayer, Wolfsthal (AT)

(73) Assignees: BAXALTA INCORPORATED, Bannockburn, IL (US); BAXALTA GMBH, Glattpark (Opfikon) (CH)

( * ) Notice: Subject to any disclaimer, the term of this patent is extended or adjusted under 35 U.S.C. 154(b) by 547 days.

(21) Appl. No.: 12/860,501

(22) Filed: Aug. 20, 2010

(65) Prior Publication Data

US 2011/0092681 A1 Apr. 21, 2011

Related U.S. Application Data

(60) Provisional application No. 61/235,570, filed on Aug. 20, 2009.

(51) Int. Cl.
*C07K 14/755* (2006.01)
*C07K 1/18* (2006.01)
*A61K 38/00* (2006.01)

(52) U.S. Cl.
CPC ............... *C07K 14/755* (2013.01); *A61K 38/00* (2013.01); *C07K 1/18* (2013.01)

(58) Field of Classification Search
None
See application file for complete search history.

(56) References Cited

U.S. PATENT DOCUMENTS

| 3,941,763 | A | 3/1976 | Sarantakis | |
|---|---|---|---|---|
| 6,465,624 | B1 | 10/2002 | Fischer et al. | |
| 6,953,837 | B2 * | 10/2005 | Mitterer et al. | 530/350 |
| 2006/0160948 | A1 | 7/2006 | Scheiflinger et al. | |

FOREIGN PATENT DOCUMENTS

WO    WO-86/06096    10/1986

OTHER PUBLICATIONS

MERCK Product Information Sheet, Fractogel® EMD SO3, downloaded from <<http://wolfson.huji.ac.il/purification/PDF/IonExchange/MERCK_SO3.pdf>> on Jul. 15, 2013.*
Alpert and Andrews, Cation-exchange chromatography of peptides on poly(2-sulfoethyl aspartamide)-silica. Journal of Chromatography, 1988, vol. 443, pp. 85-96 (Only abstract provided).*
Tosoh Bioscience webpage, <<http://www.separations.us.tosohbioscience.com/ServiceSupport/TechSupport/ResourceCenter/PrinciplesofChromatography/IonExchange>>.*
BioRad, Chromatography: Media and Columns, 2007.*
Tabb, An algorithm for isoelectric point estimation, 2003, downloaded from <<http://fields.scripps.edu/DTASelect/20010710-pl-Algorithm.pdf>>.*
Levene and Simms, Calculation of Isoelectric Points, 1923, Journal of Biological Chemistry, vol. 55, No. 4, pp. 801-813.*
Davis et al., Preparation and characterization of antibodies with specificity for the amino-terminal tetrapeptide sequence of the platelet-derived connective tissue activating peptide-III. *Biochem. Intl.* 10:395-404 (1985).
Fernandes et al., Polysialylated asparaginase: preparation, activity and pharmacokinetics. *Biochim. Biophys. Acta* 1341(1):26-34 (1997).
International Conference on Harmonisation; guidance on viral safety evaluation of biotechnology products derived from cell lines of human or animal origin; availability—FDA. Notice. *Fed. Regist.*, 63(185): 51074-4 (1998).
Lankhof et al., von Willebrand factor without the A2 domain is resistant to proteolysis. *Thromb. Haemost.* 77:1008-13 (1997).
Leyte et al., The pro-polypeptide of von Willebrand factor is required for the formation of a functional factor VIII-binding site on mature von Willebrand factor. *Biochem. J.* 274:257-61 (1991).
Merrifield, Solid phase peptide synthesis. I. The synthesis of a tetrapeptide. *J. Am. Chem. Soc.* 85:2149 (1963).
Migneault et al., Glutaraldehyde: behavior in aqueous solution, reaction with proteins, and application to enzyme crosslinking. *Biotechniques*, 37:790-6 (2004).
Pietu et al., Production in *Escherichia coli* of a biologically active subfragment of von Willebrand factor corresponding to the platelet glycoprotein Ib, collagen and heparin binding domains. Biochem. Biophys. Res. Commun. 164: 1339-47 (1989).
Ruggeri et al., von Willebrand factor. *FASEB J.* 7(2):308-16 (1993).
Saenko et al., Strategies towards a longer acting factor VIII. *Haemophilia*, 12:42-51 (2006).
Bollag et al., Chapter 9: Ion Exhange Chromatography, Protein Methods, ($2^{nd}$ Edition), pp. 231-239 (1996).
Cameron et al., The removal of model viruses poliovirus type 1 and canine parvovirus, during the purification of human albumin using ion-exchange chromatographic procedures. *J. Int. Assoc. Biol. Standard.* 25(4): 391-401 (1997).
Chandra et al., Effectiveness of alternative treatment for reducing potential viral comtaminants from plasma-derived products. *Thromb. Res.* 105(5): 391-400 (2002).
Prowse et al., Properties of pathogen-interacted plasma components. *Transf. Med. Rev.* 23(2): 124-33 (2009).
Solheim et al., Pathogen reduction of blood components. *Transfus. Apheresis Sci.* 39(1): 75- 82 (2008).
International Search Report and Written Opinion of the International Searching Authority, PCT/US2010/046180, European Patent Office, dated Nov. 18, 2010.

* cited by examiner

*Primary Examiner* — Benjamin P Blumel
(74) *Attorney, Agent, or Firm* — Marshall, Gerstein & Borun LLP

(57) ABSTRACT

The present invention provides methods for purifying Von Willebrand factor (VWF) for increased removal of non-lipid enveloped viruses.

9 Claims, 5 Drawing Sheets

A) Silver stain  B) Western blot for residual rFVIII

PURIFICATION OF VWF FOR INCREASED REMOVAL OF NON-LIPID ENVELOPED VIRUSES

CROSS-REFERENCE TO RELATED APPLICATIONS

This application claims the priority benefit under 35 U.S.C. §119(e) of U.S. Provisional Application No. 61/235,570, filed Aug. 20, 2009, the disclosure of which is incorporated herein by reference in its entirety.

FIELD OF THE INVENTION

Generally, the invention relates to methods of purifying VWF for increased removal of non-lipid enveloped viruses.

BACKGROUND OF THE INVENTION

Von Willebrand factor (VWF) is a glycoprotein circulating in plasma as a series of multimers ranging in size from about 500 to 20,000 kD. Multimeric forms of VWF are composed of 250 kD polypeptide subunits linked together by disulfide bonds. VWF mediates initial platelet adhesion to the sub-endothelium of the damaged vessel wall. Only the larger multimers exhibit hemostatic activity. It is assumed that endothelial cells secrete large polymeric forms of VWF and those forms of VWF which have a low molecular weight (low molecular weight VWF) arise from proteolytic cleavage. The multimers having large molecular masses are stored in the Weibel-Pallade bodies of endothelial cells and liberated upon stimulation.

VWF is synthesized by endothelial cells and megakaryocytes as prepro-VWF that consists to a large extent of repeated domains. Upon cleavage of the signal peptide, pro-VWF dimerizes through disulfide linkages at its C-terminal region. The dimers serve as protomers for multimerization, which is governed by disulfide linkages between the free end termini. The assembly to multimers is followed by the proteolytic removal of the propeptide sequence (Leyte et al., Biochem. J. 274 (1991), 257-261).

The primary translation product predicted from the cloned cDNA of VWF is a 2813-residue precursor polypeptide (pre-pro-VWF). The prepro-VWF consists of a 22 amino acid signal peptide and a 741 amino acid propeptide, with the mature VWF comprising 2050 amino acids (Ruggeri Z. A., and Ware, J., FASEB J., 308-316 (1993)).

Defects in VWF are causal to Von Willebrand disease (VWD), which is characterized by a more or less pronounced bleeding phenotype. VWD type 3 is the most severe form in which VWF is completely missing, and VWD type 1 relates to a quantitative loss of VWF and its phenotype can be very mild. VWD type 2 relates to qualitative defects of VWF and can be as severe as VWD type 3. VWD type 2 has many sub forms, some being associated with the loss or the decrease of high molecular weight multimers. Von Willebrand syndrome type 2a (VWS-2A) is characterized by a loss of both intermediate and large multimers. VWS-2B is characterized by a loss of highest-molecular-weight multimers. Other diseases and disorders related to VWF are known in the art.

The removal or inactivation of non-lipid enveloped viruses from therapeutic protein solutions has traditionally been accomplished by treatment with physical methods like high temperature (e.g., dry heat, vapor heat, pasteurization), irradiation with high energy rays (e.g., ultraviolet (UV) rays or beta radiation), low pH, nanofiltration or by chromatographic procedures, in particular affinity chromatography. However, these procedures are often ineffective when purifying a high molecular weight protein such as VWF which does not pass through a nanofilter and/or loses its potency or molecular integrity upon treatment with heat or radiation.

Current regulatory guidelines ask manufacturers to address the issue of reduction and/or inactivation of both lipid enveloped and non-lipid enveloped viruses for recombinant pharmaceutical products. The ICH "Guideline on Viral Safety Evaluations of Biotechnology Products" (Federal Register, 1998, 63(185): 51074-51084) gives manufacturers flexibility how to address viral issues taking into account the type of product, the production process and the risk of potentially contaminating viruses. These guidelines point out that the risk of viral contamination is a feature common to all biotechnology products derived from cell lines. Such contamination could have serious clinical consequences and can arise from the contamination of the source cell lines themselves (cell substrates) or from adventitious introduction of virus during production.

Whereas the inactivation of lipid-enveloped viruses can be performed very effectively by a solvent/detergent (S/D) treatment approach, the inactivation or removal of non-lipid-enveloped model viruses (NLEV's) can be challenging due to their small size and physical stability.

Thus there exists a need in the art to develop methods to efficiently inactivate or remove non-lipid enveloped viruses during the purification of VWF.

SUMMARY OF THE INVENTION

The present invention provides an efficient method for purifying VWF for increased removal of non-lipid enveloped viruses. The present invention provides a novel method of purifying VWF for increased removal of NLEV's by performing the product loading step and the wash step of the purification process at a high pH.

One method known in the art for purifying polypeptides from NLEV's involves the use of nanofiltration. The principle behind efficient separation of protein and virus using nanofiltration exploits the size difference between the polypeptide and the virus; efficient separation requires the polypeptide to have an effective size smaller that the virus, which allows the polypeptide to pass through the pores of the nanofilter while the virus is retained. If the polypeptide and virus are of a comparable size relative to each other, however, separation is problematic because either the polypeptide and virus both pass through the nanofilter pores or neither do. The methods disclosed herein overcome this problem by using a cation exchange resin rather than nanofiltration and loading and/or washing the resin at a sufficiently high pH to separate the polypeptide from the virus.

Without being bound by theory, the methods disclosed herein are useful for improved removal of NLEV from polypeptide solutions wherein the polypeptide is of a certain size and/or conformation. A polypeptide of a sufficiently large size is likely to have localized charge characteristics at or above the isoelectric point of the polypeptide, i.e., regions of the polypeptide can maintain localized positive or negative charges, thereby allowing the polypeptide to adsorb to the column resin while the virus flows through. This uneven charge distribution over the length of a polypeptide allows the polypeptide to remain attached to, the resin despite loading and/or washing of the resin at a high pH.

The invention provides a method for removing a non-lipid enveloped virus from a protein-containing solution comprising loading a protein in the solution onto a cation exchange resin, and washing the resin with a buffer at a pH higher than the isoelectric point of the protein to elute the virus. In one aspect, the protein is loaded onto the resin in a buffer at a pH higher than that of the isoelectric point of the protein to elute the virus. In another aspect, the protein is loaded onto the resin in a buffer that is not the buffer used in the wash step, and the resin is subsequently washed with the buffer that is at a pH higher than an isoelectric point of the protein.

In one embodiment, a method for removing a non-lipid enveloped virus from a protein-containing solution is provided comprising applying the solution to a cation exchange resin at a pH higher than the isoelectric point of the protein, and washing the cation exchange resin with a first wash buffer to form an eluate, said first wash buffer having a pH that is equal to or lower than the solution applied to the cation exchange resin.

In one aspect, the pH of the solution is about 1 pH unit above the isoelectric point of the protein. In other aspects, the pH of the solution is about 1.1, or about 1.2, or about 1.3, or about 1.4, or about 1.5, or about 1.6, or about 1.7, or about 1.8, or about 1.9, or about 2.0, or about 2.1, or about 2.2, or about 2.3, or about 2.4, or about 2.5, or about 2.6, or about 2.7, or about 2.8, or about 2.9, or about 3.0, or about 3.1, or about 3.2, or about 3.3, or about 3.4, or about 3.5, or about 3.6, or about 3.7, or about 3.8, or about 3.9, or about 4.0, or about 4.1, or about 4.2, or about 4.3, or about 4.4, or about 4.5, or about 4.6, or about 4.7, or about 4.8, or about 4.9, or about 5.0, or about 5.1, or about 5.2, or about 5.3, or about 5.4, or about 5.5, or about 5.6, or about 5.7, or about 5.8, or about 5.9, or about 6.0 or more pH units or more above the isoelectric point of the protein. In these embodiments, the pH is greater than about 7. In a related aspect, the pH of the protein-containing solution is about 7.0. In other aspects, the pH of the protein-containing solution is about 7.1, or about 7.2, or about 7.3, or about 7.4, or about 7.5, or about 7.6, or about 7.7, or about 7.8, or about 7.9, or about 8.0, or about 8.1, or about 8.2, or about 8.3, or about 8.4, or about 8.5, or about 8.6, or about 8.7, or about 8.8, or about 8.9, or about 9.0, or about 9.1, or about 9.2, or about 9.3, or about 9.4, or about 9.5, or about 9.6, or about 9.7, or about 9.8, or about 9.9, or about 10.0, or about 10.1, or about 10.2, or about 10.3, or about 10.4, or about 10.5, or about 10.6, or about 10.7, or about 10.8, or about 10.9, or about 11.0, or about 11.1, or about 11.2, or about 11.3, or about 11.4, or about 11.5, or about 11.6, or about 11.7, or about 11.8, or about 11.9, or about 12.0, or about 12.1, or about 12.2, or about 12.3, or about 12.4, or about 12.5, or about 12.6, or about 12.7, or about 12.8, or about 12.9, or about 13.0 or higher.

In another embodiment, a method is provided for removing a non-lipid enveloped virus from a protein-containing solution comprising applying the solution to a cation exchange resin, washing the cation exchange resin with a first wash buffer at a pH higher than the pH of the solution applied to the cation exchange resin, and washing the cation exchange resin with a second wash buffer to form an eluate, said first eluant having a pH that is equal to or lower than the first wash buffer. In one aspect, the pH of the first wash buffer is about 1 pH unit above the pH of the solution applied to the cation exchange resin. In other aspects, the pH of the first wash buffer is about 0.1, or about 0.2, or about 0.3, or about 0.4, or about 0.5, or about 0.6, or about 0.7, or about 0.8, or about 0.9, or about 1.1, or about 1.2, or about 1.3, or about 1.4, or about 1.5, or about 1.6, or about 1.7, or about 1.8, or about 1.9, or about 2.0, or about 2.1, or about 2.2, or about 2.3, or about 2.4, or about 2.5, or about 2.6, or about 2.7, or about 2.8, or about 2.9, or about 3.0, or about 3.1, or about 3.2, or about 3.3, or about 3.4, or about 3.5, or about 3.6, or about 3.7, or about 3.8, or about 3.9, or about 4.0, or about 4.1, or about 4.2, or about 4.3, or about 4.4, or about 4.5, or about 4.6, or about 4.7, or about 4.8, or about 4.9, or about 5.0, or about 5.1, or about 5.2, or about 5.3, or about 5.4, or about 5.5, or about 5.6, or about 5.7, or about 5.8, or about 5.9, or about 6.0, or about 6.1, or about 6.2, or about 6.3, or about 6.4, or about 6.5, or about 6.6, or about 6.7, or about 6.8. or about 6.9, or about 7.0, or about 7.1, or about 7.2, or about 7.3, or about 7.4, or about 7.5, or about 7.6, or about 7.7, or about 7.8, or about 7.9, or about 8 or about 8.1, or about 8.2, or about 8.3, or about 8.4, or about 8.5, or about 8.6, or about 8.7, or about 8.8, or about 8.9, or about 9, or about 9.1, or about 9.2, or about 9.3, or about 9.4, or about 9.5, or about 9.6, or about 9.7, or about 9.8, or about 9.9, or about 10 or more pH units or more above the isoelectric point of the protein. In these embodiments, the pH of the first wash buffer is greater than about 7. In other aspects, the pH of the first wash buffer is about 7.1, or about 7.2, or about 7.3, or about 7.4, or about 7.5, or about 7.6, or about 7.7, or about 7.8, or about 7.9, or about 8.0, or about 8.1, or about 8.2, or about 8.3, or about 8.4, or about 8.5, or about 8.6, or about 8.7, or about 8.8, or about 8.9, or about 9.0, or about 9.1, or about 9.2, or about 9.3, or about 9.4, or about 9.5, or about 9.6, or about 9.7, or about 9.8, or about 9.9, or about 10.0, or about 10.1, or about 10.2, or about 10.3, or about 10.4, or about 10.5, or about 10.6, or about 10.7, or about 10.8, or about 10.9, or about 11.0 or higher.

In an embodiment, the protein in the solution is a polypeptide having a molecular mass of at least about 150 kilodaltons. In various aspects, the protein in the solution is a polypeptide having a molecular mass of at least about 175 kilodaltons, or about 180 kilodaltons, or about 190 kilodaltons, or about 200 kilodaltons, or about 210 kilodaltons, or about 220 kilodaltons, or about 230 kilodaltons, or about 240 kilodaltons, or about 250 kilodaltons, or about 260 kilodaltons, or about 270 kilodaltons, or about 280 kilodaltons, or about 290 kilodaltons, or about 300 kilodaltons, or about 310 kilodaltons, or about 320 kilodaltons, or about 330 kilodaltons, or about 340 kilodaltons, or about 350 kilodaltons, or about 360 kilodaltons, or about 370 kilodaltons, or about 380 kilodaltons, or about 390 kilodaltons, or about 400 kilodaltons, or about 410 kilodaltons, or about 420 kilodaltons, or about 430 kilodaltons, or about 440 kilodaltons, or about 450 kilodaltons, or about 460 kilodaltons, or about 470 kilodaltons, or about 480 kilodaltons, or about 490 kilodaltons, or about 500 kilodaltons or more. As described herein, polypeptides also comprise multimeric structures and such multimeric structures, in various aspects, have a molecular mass of at least about 500 kilodaltons. In related aspects, the multimeric structures have a molecular mass of at least about 510, or about 520, or about 530, or about 540, or about 550, or about 560, or about 570, or about 580, or about 590, or about 600, or about 610, or about 620, or about 630, or about 640, or about 650, or about 660, or about 670, or about 680, or about 690, or about 700, or about 710, or about 720, or about 730, or about 740, or about 750, or about 760, or about 770, or about 780, or about 790, or about 800, or about 810, or about 820, or about 830, or about 840, or about 850, or about 860, or about 870, or about 880, or about 890, or about 900, or about 910, or about 920, or about 930, or about 940, or about 950, or about 960, or about 970, or about 980, or about 990 kilodaltons, or about 1 megadalton, or about 1.1 megadaltons, or about 1.2 megadaltons, or about 1.3 megadaltons, or about 1.4 megadaltons, or about 1.5 megadaltons, or about 1.6 megadaltons, or about 1.7 megadaltons, or about 1.8 megadaltons, or about 1.9 megadaltons, or about 2.0 megadaltons, or about 2.1 megadaltons, or about 2.2 megadaltons, or about 2.3 megadaltons, or about 2.4 megadaltons, or about 2.5 megadaltons, or about 2.6 megadaltons, or about 2.7 megadaltons, or about 2.8 megadaltons, or about 2.9 megadaltons, or about 3.0 megadaltons, or about 3.1 megadaltons, or about 3.2 megadaltons, or about 3.3 megadaltons, or about 3.4 megadaltons, or about 3.5 megadaltons, or about 3.6 megadaltons, or about 3.7 megadaltons, or about 3.8 megadaltons, or about 3.9 megadaltons, or about 4.0 megadaltons, or about 4.1 megadaltons, or about 4.2 megadaltons, or about 4.3 megadaltons, or about 4.4 megadaltons, or about 4.5 megadaltons, or about 4.6 megadaltons, or about 4.7 megadaltons, or about 4.8 megadaltons, or about 4.9 megadaltons, or about 5.0 megadaltons or more.

In some embodiments, the cation exchange resin has a negatively charged group selected from the group consisting of carboxymethyl (CM), sulphoalkyl (SP, SE), sulphate and methylsulfonate (S) as well as any other negatively charged ligand.

In a further embodiment, the protein is a blood coagulation protein. In various aspects, the blood coagulation protein is selected from the group consisting of Factor VIII, von Willebrand factor, FI (Fibrinogen), FV (Proaccelerin), FXI (plasma-thromboplastin antecedent), and FXIII (fibrin stabilizing factor).

In an embodiment, a method for removing a non-lipid enveloped virus from a von Willebrand (VWF)-containing solution is provided comprising applying the solution to a cation exchange resin at a pH higher than the isoelectric point of the protein and washing the cation exchange resin with a first wash buffer to form an eluate, said first wash buffer having a pH that is equal to or lower than the solution applied to the cation exchange resin.

In another embodiment, a method for removing a non-lipid enveloped virus from a VWF-containing solution is provided comprising applying the solution to a cation exchange resin, washing the cation exchange resin with a first wash buffer at a pH higher than the pH of the solution applied to the cation exchange resin and washing the cation exchange resin with a second wash buffer to form an eluate, said first eluant having a pH that is equal to or lower than the first wash buffer.

In a further embodiment, a method for removing a non-lipid enveloped virus from a VWF-containing solution comprising applying the solution to a cation exchange resin at a pH higher than the isoelectric point of the protein and washing the cation exchange resin with a first wash buffer at a pH higher than the isoelectric point of the protein applied to the cation exchange resin; and washing the cation exchange resin with a second wash buffer to form an eluate, said first eluant having a pH that is equal to or lower than the first wash buffer.

DETAILED DESCRIPTION OF THE INVENTION

Figure 1:
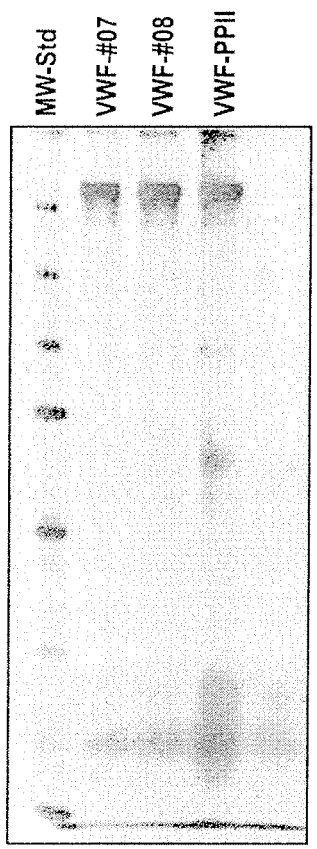
FIG. 1 shows the result of an SDS-PAGE separation followed by silver staining (A) and Western Blot (B) analysis for residual rFVIII.
Figure 1:
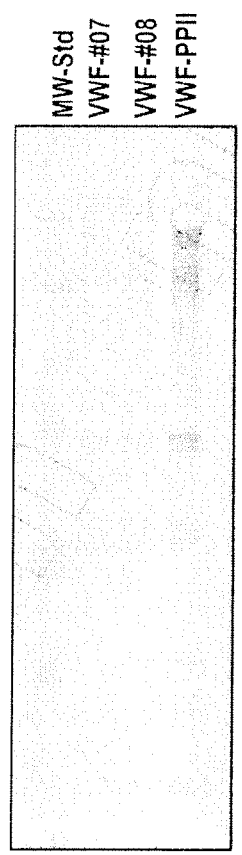

The present invention relates to a method for purifying VWF with increased removal of non-lipid enveloped viruses.

The methods of the invention are applicable in column (i.e., chromatography) as well as batch (i.e., without column hardware) mode.

The method of the present invention utilizes a purification method on a cation exchange resin for the increased removal of non-lipid enveloped viruses. Previous methods of purification of VWF using cation exchange chromatography were performed at a neutral pH. These methods allowed for the manufacture of purified VWF of good yield and purity, but surprisingly the process had no capacity to remove non-lipid enveloped viruses.

DEFINITION OF TERMS

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

As used herein, the following terms have the meanings ascribed to them unless specified otherwise.

As used herein the terms "express," "expressing" and "expression" mean allowing or causing the information in a gene or DNA sequence to become manifest, for example, producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed." An expression product can be characterized as intracellular, extracellular or secreted. The term "intracellular" means inside a cell. The term "extracellular" means outside a cell, e.g., certain types of transmembrane proteins. A substance is "secreted" by a cell if it appears in significant measure outside the cell, from somewhere on or inside the cell.

As used herein a "polypeptide" refers to a polymer composed of amino acid residues, structural variants, related naturally-occurring structural variants, and synthetic non-naturally occurring analogs thereof linked via peptide bonds. Synthetic polypeptides can be prepared, for example, using an automated polypeptide synthesizer. The term "protein" typically refers to large polypeptides. The term "peptide" typically refers to short polypeptides. The term "polypeptide" also includes polymeric structures. Therefore, a "polypeptide" may be a monomer, dimer, trimer, or larger multimeric structure. These multimeric structures can be up to 5 megadaltons or larger.

As used herein, the "isoelectric point" is the pH value at which the net electric charge of a polypeptide in an aqueous solution is zero.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution of one or more amino acids for other amino acids. Substitutions can be conservative or non-conservative based on the physico-chemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate the molecule's solubility, absorption, biological half-life, etc. The moieties may alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example, the variant may be a blood clotting factor having a chemical modification which confers a longer half-life in vivo to the protein. In various aspects, polypeptides are modified by glycosylation, pegylation, and/or polysialylation.

Recombinant VWF

The polynucleotide and amino acid sequences of prepro-VWF are set out in SEQ ID NO:1 and SEQ ID NO:2, respectively, and are available at GenBank Accession Nos. NM_000552 and NP_000543, respectively. The amino acid sequence corresponding to the mature VWF protein is set out in SEQ ID NO: 3 (corresponding to amino acids 764-2813 of the full length prepro-VWF amino acid sequence).

One form of useful rVWF has at least the property of in vivo-stabilizing, e.g. binding, of at least one Factor VIII (FVIII) molecule and having optionally a glycosylation pattern which is pharmacologically acceptable. Specific examples thereof include VWF without A2 domain thus resistant to proteolysis (Lankhof et al., Thromb. Haemost. 77: 1008-1013, 1997), and the VWF fragment from Val 449 to Asn 730 including the glycoprotein Ib-binding domain and binding sites for collagen and heparin (Pietu et al., Biochem. Biophys. Res. Commun. 164: 1339-1347, 1989). The determination of the ability of a VWF to stabilize at least one FVIII molecule can be carried out in VWF-deficient mammals according to methods known in the state in the art.

The rVWF of the present invention may be produced by any method known in the art. One specific example is disclosed in WO86/06096 published on Oct. 23, 1986 and U.S. patent application Ser. No. 07/559,509, filed on Jul. 23, 1990, which is incorporated herein by reference with respect to the methods of producing recombinant VWF. Thus, methods are known in the art for (i) the production of recombinant DNA by genetic engineering, e.g. via reverse transcription of RNA and/or amplification of DNA, (ii) introducing recombinant DNA into procaryotic or eucaryotic cells by transfection, e.g. via electroporation or microinjection, (iii) cultivating said transformed cells, e.g. in a continuous or batchwise manner, (iv) expressing VWF, e.g. constitutively or upon induction, and (v) isolating said VWF, e.g. from the culture medium or by harvesting the transformed cells, in order to (vi) obtain purified rVWF, e.g. via anion exchange chromatography or affinity chromatography. A recombinant VWF may be made in transformed host cells using recombinant DNA techniques well known in the art. For instance, sequences coding for the polypeptide could be excised from DNA using suitable restriction enzymes.

Alternatively, the DNA molecule could be synthesized using chemical synthesis techniques, such as the phosphoramidate method. Also, a combination of these techniques could be used.

The invention also provides vectors encoding polypeptides of the invention in an appropriate host. The vector comprises the polynucleotide that encodes the polypeptide operatively linked to appropriate expression control sequences. Methods of effecting this operative linking, either before or after the polynucleotide is inserted into the vector, are well known. Expression control sequences include promoters, activators, enhancers, operators, ribosomal binding sites, start signals, stop signals, cap signals, polyadenylation signals, and other signals involved with the control of transcription or translation. The resulting vector having the polynucleotide therein is used to transform an appropriate host. This transformation may be performed using methods well known in the art.

Any of a large number of available and well-known host cells may be used in the practice of this invention. The selection of a particular host is dependent upon a number of factors recognized by the art, including, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all host cells are equally effective for the expression of a particular DNA sequence. Within these general guidelines, useful microbial host cells include bacteria, yeast and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the polypeptides are purified from culture by methods well known in the art.

Depending on the host cell utilized to express a compound of the invention, carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Alternatively, the compounds may be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides.

Fragments, Variants and Analogs of VWF

Methods for preparing polypeptide fragments, variants or analogs are well-known in the art.

Fragments of a polypeptide are prepared using, without limitation, enzymatic cleavage (e.g., trypsin, chymotrypsin) and also using recombinant means to generate a polypeptide fragments having a specific amino acid sequence. Polypeptide fragments may be generated comprising a region of the protein having a particular activity, such as a multimerization domain or any other identifiable VWF domain known in the art.

Variants of a polypeptide are contemplated to include human and non-human forms of VWF (e.g., murine VWF). Also contemplated by the methods herein are chimeric polypeptides comprising, e.g., a mouse/human fusion polypeptide.

Methods of making polypeptide analogs are also well-known. Amino acid sequence analogs of a polypeptide can be substitutional, insertional, addition or deletion analogs. Deletion analogs, including fragments of a polypeptide, lack one or more residues of the native protein which are not essential for function or immunogenic activity. Insertional analogs involve the addition of, e.g., amino acid(s) at a non-terminal point in the polypeptide. This analog may include insertion of an immunoreactive epitope or simply a single residue. Addition analogs, including fragments of a polypeptide, include the addition of one or more amino acids at either of both termini of a protein and include, for example, fusion proteins.

Substitutional analogs typically exchange one amino acid of the wild-type for another at one or more sites within the protein, and may be designed to modulate one or more properties of the polypeptide without the loss of other functions or properties. In one aspect, substitutions are conservative substitutions. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

Analogs may be substantially homologous or substantially identical to the recombinant VWF from which they are derived. Preferred analogs are those which retain at least some of the biological activity of the wild-type polypeptide, e.g. blood clotting activity.

Polypeptide variants contemplated include polypeptides chemically modified by such techniques as ubiquitination, glycosylation, including polysialation, conjugation to therapeutic or diagnostic agents, labeling, covalent polymer attachment such as pegylation (derivatization with polyethylene glycol), introduction of non-hydrolyzable bonds, and insertion or substitution by chemical synthesis of amino acids such as ornithine, which do not normally occur in human proteins. Variants retain the same or essentially the same binding properties of non-modified molecules of the invention. Such chemical modification may include direct or indirect (e.g., via a linker) attachment of an agent to the VWF polypeptide. In the case of indirect attachment, it is contemplated that the linker may be hydrolyzable or non-hydrolyzable.

Preparing pegylated polypeptide analogs will generally comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-pegylated product. In some embodiments, the binding construct will have a single PEG moiety at the N-terminus. Polyethylene glycol (PEG) may be attached to the blood clotting factor to provide a longer half-life in vivo. The PEG group may be of any convenient molecular weight and may be linear or branched. The average molecular weight of the PEG ranges from about 2 kiloDalton ("kD") to about 100 kDa, from about 5 kDa to about 50 kDa, or from about 5 kDa to about 10 kDa. The PEG groups are attached to the blood clotting factor via acylation or reductive alkylation through a natural or engineered reactive group on the PEG moiety (e.g., an aldehyde, amino, thiol, or ester group) to a reactive group on the blood clotting factor (e.g., an aldehyde, amino, or ester group) or by any other technique known in the art.

Methods for preparing polysialylated polypeptide are described in United States Patent Publication 20060160948, Fernandes et Gregoriadis; Biochim. Biophys. Acta 1341: 26-34, 1997, and Saenko et al., Haemophilia 12:42-51, 2006. Briefly, a solution of colominic acid containing 0.1 M $NaIO_4$ is stirred in the dark at room temperature to oxidize the CA. The activated CA solution is dialyzed against, e.g., 0.05 M sodium phosphate buffer, pH 7.2 in the dark and this solution was added to a rVWF solution and incubated for 18 h at room temperature in the dark under gentle shaking. Free reagents can then be separated from the rVWF-polysialic acid conjugate by ultrafiltration/diafiltration. Conjugation of rVWF with polysialic acid may also be achieved using glutaraldehyde as cross-linking reagent (Migneault et al., Biotechniques 37: 790-796, 2004).

It is further contemplated that a polypeptide of the invention may be a fusion protein with a second agent which is a polypeptide. In one embodiment, the second agent which is a polypeptide, without limitation, is an enzyme, a growth factor, an antibody, a cytokine, a chemokine, a cell-surface receptor, the extracellular domain of a cell surface receptor, a cell adhesion molecule, or fragment or active domain of a protein described above. In a related embodiment, the second agent is a blood clotting factor such as Factor VIII, Factor VII, Factor IX. The fusion protein contemplated is made by chemical or recombinant techniques well-known in the art.

It is also contemplated that prepro-VWF and pro-VWF polypeptides may provide a therapeutic benefit in the formulations of the present invention. For example, U.S. Pat. No. 7,005,502 describes a pharmaceutical preparation comprising substantial amounts of pro-VWF that induces thrombin generation in the presence of platelets in vitro. In addition to recombinant, biologically active fragments, variants, or analogs of the naturally-occurring mature VWF, the present invention contemplates the use of recombinant biologically active fragments, variants, or analogs of the prepro-VWF (set out in SEQ ID NO:2) or pro-VWF polypeptides (amino acid residues 23 to 764 of SEQ ID NO: 2) in the formulations described herein.

Polynucleotides encoding fragments, variants and analogs may be readily generated by a worker of skill to encode biologically active fragments, variants, or analogs of the naturally-occurring molecule that possess the same or similar biological activity to the naturally-occurring molecule. These polynucleotides can be prepared using PCR techniques, digestion/ligation of DNA encoding molecule, and the like. Thus, one of skill in the art will be able to generate single base changes in the DNA strand to result in an altered codon and a missense mutation, using any method known in the art, including, but not limited to site-specific mutagenesis. As used herein, the phrase "moderately stringent hybridization conditions" means, for example, hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47-9.51 in Molecular Cloning, Cold Spring Harbor Laboratory Press, Cold Spring Harbor, N.Y. (1989).

Methods of Producing VWF

Industrially, VWF, in particular human recombinant VWF (rVWF), is synthesized and expressed together with rFVIII in a genetically engineered CHO cell line. The function of the co-expressed rVWF is to stabilize rFVIII in the cell culture process. rVWF is synthesized in the cell as the pro-form, containing a large pro-peptide attached to the N-terminus. Upon maturation in the endoplasmatic reticulum and Golgi apparatus, the pro-peptide is cleaved off by the action of the cellular protease furin and is secreted as a homopolymer of identical subunits, consisting of dimers of the expressed protein.

Purification of VWF

Provided herein is a method for removing a non-lipid enveloped virus from a protein-containing solution is provided comprising applying the solution to a cation exchange resin at a pH higher that the isoelectric point of the protein, and washing the cation exchange resin with a first wash buffer to form an eluate, said first wash buffer having a pH that is equal to or lower than the solution applied to the cation exchange resin.

In one aspect, the pH of the solution is about 1 pH unit above the isoelectric point of the protein. In other aspects, the pH of the solution is about 1.2, or about 1.4, or about 1.6, or about 1.8, or about 2.0, or about 2.2, or about 2.4, or about 2.6, or about 2.8, or about 3.0, or about 3.2, or about 3.4, or about 3.6, or about 3.8, or about 4.0, or about 4.2, or about 4.4, or about 4.6, or about 4.8, or about 5.0, or about 5.5, or about 6.0 pH units or more above the isoelectric point of the protein.

In these embodiments, the pH is greater than about 7. In other aspects, the pH is about 7.1, or about 7.2, or about 7.3, or about 7.4, or about 7.5, or about 7.6, or about 7.7, or about 7.8, or about 7.9, or about 8.0, or about 8.1, or about 8.2, or about 8.3, or about 8.4, or about 8.5, or about 8.6, or about 8.7, or about 8.8, or about 8.9, or about 9.0, or about 9.1, or about 9.2, or about 9.3, or about 9.4, or about 9.5, or about 9.6, or about 9.7, or about 9.8, or about 9.9, or about 10.0, or about 10.1, or about 10.2, or about 10.3, or about 10.4, or about 10.5, or about 10.6, or about 10.7, or about 10.8, or about 10.9, or about 11.0, or about 11.1, or about 11.2, or about 11.3, or about 11.4, or about 11.5, or about 11.6, or about 11.7, or about 11.8, or about 11.9, or about 12.0, or about 12.1, or about 12.2, or about 12.3, or about 12.4, or about 12.5, or about 12.6, or about 12.7, or about 12.8, or about 12.9, or about 13.0 or higher.

In another embodiment, a method is provided for removing a non-lipid enveloped virus from a protein-containing solution comprising applying the solution to a cation exchange resin, washing the cation exchange resin with a first wash buffer at a pH higher than the pH of the solution applied to the cation exchange resin, and washing the cation exchange resin with a second wash buffer to form an eluate, said second wash buffer having a pH that is equal to or lower than the first wash buffer. In one aspect, the pH of the first wash buffer is about 1 pH unit above the pH of the solution applied to the cation exchange resin. For this stage it is contemplated that the ion exchange media is UNOsphere™ S (BioRad Laboratories, Inc., Hercules, Calif.), but other cation exchange systems may be used in the practice of the methods. These cation exchange systems are known to those of ordinary skill in the art.

In other aspects, the pH of the first wash buffer is about 1.1, or about 1.2, or about 1.3, or about 1.4, or about 1.5, or about 1.6, or about 1.7, or about 1.8, or about 1.9, or about 2.0, or about 2.1, or about 2.2, or about 2.3, or about 2.4, or about 2.5, or about 2.6, or about 2.7, or about 2.8, or about 2.9, or about 3.0, or about 3.1, or about 3.2, or about 3.3, or about 3.4, or about 3.5, or about 3.6, or about 3.7, or about 3.8, or about 3.9, or about 4.0, or about 4.1, or about 4.2, or about 4.3, or about 4.4, or about 4.5, or about 4.6, or about 4.7, or about 4.8, or about 4.9, or about 5.0, or about 5.1, or about 5.2, or about 5.3, or about 5.4, or about 5.5, or about 5.6, or about 5.7, or about 5.8, or about 5.9, or about 6.0 pH units or more above the isoelectric point of the protein. In these embodiments, the pH of the first wash buffer is greater than about 7. In other aspects, the pH of the first wash buffer is about 7.1, or about 7.2, or about 7.3, or about 7.4, or about 7.5, or about 7.6, or about 7.7, or about 7.8, or about 7.9, or about 8.0, or about 8.1, or about 8.2, or about 8.3, or about 8.4, or about 8.5, or about 8.6, or about 8.7, or about 8.8, or about 8.9, or about 9.0, or about 9.1, or about 9.2, or about 9.3, or about 9.4, or about 9.5, or about 9.6, or about 9.7, or about 9.8, or about 9.9, or about 10.0, or about 10.1, or about 10.2, or about 10.3, or about 10.4, or about 10.5, or about 10.6, or about 10.7, or about 10.8, or about 10.9, or about 11.0, or about 11.1, or about 11.2, or about 11.3, or about 11.4, or about 11.5, or about 11.6, or about 11.7, or about 11.8, or about 11.9, or about 12.0, or about 12.1, or about 12.2, or about 12.3, or about 12.4, or about 12.5, or about 12.6, or about 12.7, or about 12.8, or about 12.9, or about 13.0 or higher.

The following examples are not intended to be limiting but only exemplary of specific embodiments of the invention.

EXAMPLES

Example 1

Viruses and Cells Used in the Assays Described Below are as Follows

REO-3 (Family Reoviridae; non-enveloped dsRNA virus), Strain Dearing (ATCC VR-824) was obtained from the ATCC. The virus was propagated and titrated on Vero cells obtained from ECACC (84113001). MMV (Family Parvoviridae; non-enveloped ssDNA virus), prototype strain (ATCC VR-1346), was obtained from the American Type Culture Collection, Rockville, Md. The virus was propagated and titrated on A9 cells (ATCC CCL-1.4). PPV (Family Parvoviridae; non-enveloped ssDNA virus), strain Tennessee (BRFF #PP951024), was obtained from Biological Research Faculty & Facility, Ijamsville, Md. The virus was propagated and titrated on PK-13 cells (ATCC CRL-6489). EMCV (Family Picornaviridae; non-enveloped ssRNA) (ATCC #VR-129B) was obtained from the American Type Culture Collection. The virus was propagated and titrated on Vero cells (European Collection of Cell Cultures, ECACC, #84113001). HadV (Family Adenoviridae; non-enveloped dsDNA), strain Adenoid 75 (ATCC VR-5), was obtained from the American Type Culture Collection. The virus was propagated and titrated on HeLa cells (ATCC CCL-2).

The steps involved in an exemplary VWF purification process comprise:

Immune affinity chromatography of cell culture supernatant
  i. Flow-through fraction
  Anion Exchange (e.g., trimethylaminoethyl anion exchange column)
  Filtration (0.45/0.2 µm)
  Anion Exchange (e.g., Mustang Q (Pall Corporation))
  Virus Inactivation (e.g., using solvent/detergent treatment)
  Filtration (0.8/0.65 µm)
  Cation Exchange (e.g., UNO S column)
  Ultrafiltration/Concentration
  Filtration (0.45/0.2 µm)
  Gel Filtration (Superose 6 prep grade (GE Life Sciences))
  Optimization of UNO S Step.

During the UNO S step rVWF is bound to a strong cation exchange resin while some of the impurities pass through. After washing the column with increased conductivity buffers the bound rVWF is released from the column with a salt step. During the initial virus removal studies, this step showed at least a significant removal rate for the model REO virus. The conditions of the applied parameters and the corresponding results are listed in Table 1, below.

TABLE 1

| Parameter | Standard value | Changed value | MMV reduction factor (log10) |
|---|---|---|---|
| Conductivity load/wash | 15 mS/cm | 25 mS/cm | n.a. |
| pH load/wash/elution | 6.5 | 8.0 | 0.9 |
| Wash buffer 2 | TQA buffer* | TQA buffer with 200 mM betaine | 0.7 |
| Wash buffer 3 | TQA buffer | TQA buffer with 20% ethylen glycol | |
| Wash buffer 4 | TQA buffer | TQA buffer with 10 mM $CaCl_2$ | 0.8 |
| Wash buffer 5 | TQA buffer | TQA buffer with 10 mM EDTA | |
| pH load/wash | 6.5 | 9.0 | 2.0, 2.11, 2.12 and 2.12 |
| pH load/wash | 6.5 | 9.0 | 2.12 for REO virus |

*TQA Buffer: Tris, NaAc, mM NaCl in WFI
pH 6.3-6.7 at 20-25° C.

As can be seen in Table 1 the moderate changes in the process parameters (modification of conductivity, pH 8.0 and additives to wash buffers) did not result in a significant improvement of the MMV removal rates. Increasing the pH further to 9.0 reproducibly resulted in a significant removal rate of more than 2 logs for MMV as well as REO virus. This process change is technically easy to implement and the exposure of rVWF to the high pH environment can be kept relatively short (max. 6 hours). Elution of the bound rVWF is performed under neutral conditions.

The analysis of the virus inactivation capacity of the processes was carried out according to the recommendations of the CPMP guideline 268/95, using the following formula:

$$R = \log\left(\frac{V_1 \times T_1}{V_2 \times T_2}\right)$$

where
R=virus reduction factor
V1=volume of starting material [ml]
T1=concentration of virus in starting material [TCID50/ml]
V2=volume of material after the step [ml]
T2=concentration of virus after the step [TCID50/ml]

The volumes and the titers of each spiked sample before and after treatment were used to calculate R. Whenever virus was undetectable, the detection limit was taken as the virus titer for calculation. Calculations were carried out with virus titers ($\log_{10}$[TCID50/ml]) given to two decimal places, and only final results, i.e. reduction factors (R), were rounded to the first decimal place.

Example 2

The UNO S eluate was concentrated to approximately 800 µg rVWF antigen/ml by ultrafiltration using 30 kDa cut-off modified cellulose membranes to facilitate the trace analysis of impurities and product variants.

Testing of rVWF
Ristocetin Activity.

The Ristocetin Cofactor Activity is determined by a turbidimetric analyzer using a von Willebrand reagent containing stabilized thrombocytes and the antibiotic "ristocetin". The von Willebrand Factor contained in the sample (=Ristocetin Cofactor) causes agglutination of stabilized thrombocytes in the presence of ristocetin. The agglutination reduces the turbidity of the reagent preparation, and the change in optical density is measured by the turbidimetric analyzer. Calibration is performed by the WHO concentrate reference standard #00/514.

VWF Antigen.

VWF-samples are tested for their content of vWF-Antigen in an ELISA assay—double sandwich system with two polyclonal antibodies. Measurement of the color reactions on the microtitre plates is performed with a photometer at 490 nm. The concentration of each sample is calculated towards the standard curve with a computer supported ELISA Analysis Program (curve algorithm:Cubic regression). All readings are corrected against the blank.

FVIII Binding Activity.

FVIII binding of rVWF under static conditions was determined by an ELISA chromogenic assay (ECA) by incubating a constant amount of rFVIII with a diluted VWF-containing sample. The VWF-FVIII-complex formed was then transferred to a microtiter plate coated with a commercially available polyclonal rabbit anti-human VWF antibody. After incubation, unbound FVIII was removed by a subsequent washing step. Bound FVIII was quantified by a commercially available FVIII chromogenic assay (Technochrom FVIII:C reagent kit, Technoclone, Austria). The blank corrected optical densities (in mOD/min at 405 nm) were plotted against the VWF:Ag concentrations in logarithmic scale.

SDS-PAGE Analysis.

Conventional 8% SDS-PAGE analysis under reducing conditions and staining of the gels with Coomassie Blue and Silver Stain can provide insight in the protein composition of rVWF. After transfer of the separated protein bands to a nitrocellulose membrane and immunological staining of the protein with appropriate antibodies against VWF, FVIII and Furin respectively, a comparison of VWF related proteins to total proteins can be made.

Multimer Analysis.

The multimeric structure of VWF is analyzed by high-density horizontal SDS agarose gel electrophoresis. In brief, samples are diluted to the same concentration in the range of 0.3-1.0 IU/ml VWF:Ag, incubated with Tris-EDTA-SDS buffer and the multimers separated under non-reducing conditions on an agarose gel. VWF multimers were visualized by in-gel immunostaining with a polyclonal rabbit anti human VWF antibody, followed by alkaline phosphatase (ALP) conjugated goat anti-rabbit IgG using the ALP color development kit. Alternatively, agarose gels were blotted onto a blotting membrane and staining was performed by a polyclonal rabbit anti-human VWF antibody followed by horse radish peroxidase conjugated anti-rabbit IgG. For visualization, electro-chemi-luminescence was used which increases the sensitivity of detection for VWF by at least two magnitudes. Low (1 agarose) and high resolution (2.5% agarose) conditions were used to analyze the size distribution of VWF multimers and the multimeric structure, respectively.

HPLC Analysis.

Recombinant VWF can be cleaved by GluC (V8 protease) under native conditions to give two main fragments (N-terminal and C-terminal homodimer fragment), which are separated on a reverse phase HPLC C4-column. The fragments are detected by monitoring the UV absorbance at 280 nm.

Peptide Mapping.

The primary structure of rVWF was investigated using a peptide mapping approach. Samples of purified rVWF were reduced with dithiothreitol (DTT) and the free, sulfhydril groups were blocked with 4-vinylpyridin. Sequencing grade trypsin was added to the rVWF and allowed to react for 18 hours. The resulting peptide mixture was separated by reverse phase chromatography. Eluting peptides were detected by on-line UV detection at 214 nm and on-line electrospray ionization mass spectrometry.

Test for Deamidated rVWF.

The analytical method for the detection of isoaspartate (one reaction product originating from the de-amidation of asparagine) employs tryptic digestion, followed by the Protein Isoaspartyl Methyltransferase (PIMT) enzymatic reaction using the ISOQUANT IsoAspartate Detection Kit supplied by Promega. PIMT catalyzes the transfer of a methyl group from the substrate S-adenosyl-L methionine (SAM) to IsoAsp at the carboxyl position, generating S-adenosyl homocysteine (SAH). The stoichiometrically released SAH is detected at a wavelength of 260 nm by a RP HPLC method.

The analytical data for the product obtained by the different processes are summarized in Table 2.

TABLE 2

Analytical Data for pH 9 and Control Runs

Figure 2:
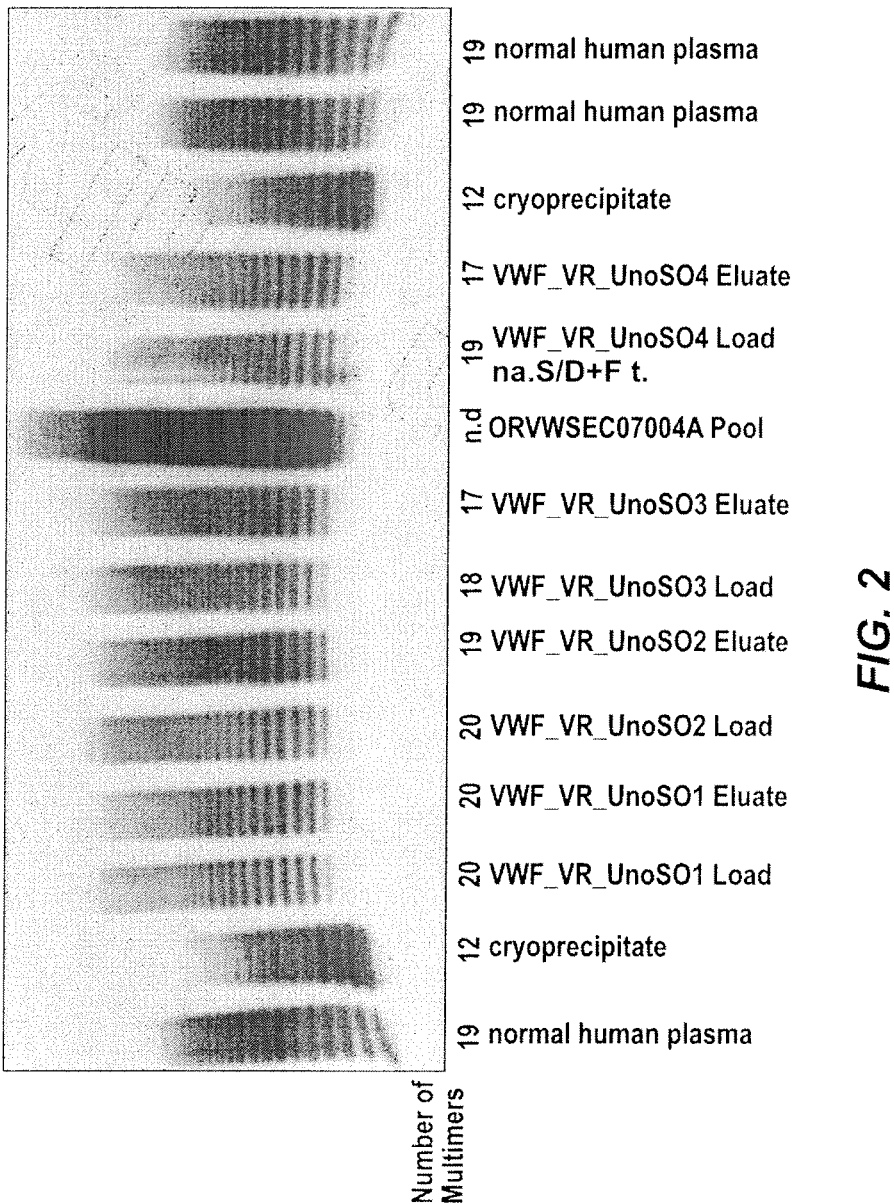
FIG. 2 shows the stained gel of the UNO S runs with MMV and REO virus spiked samples.
Figure 3:
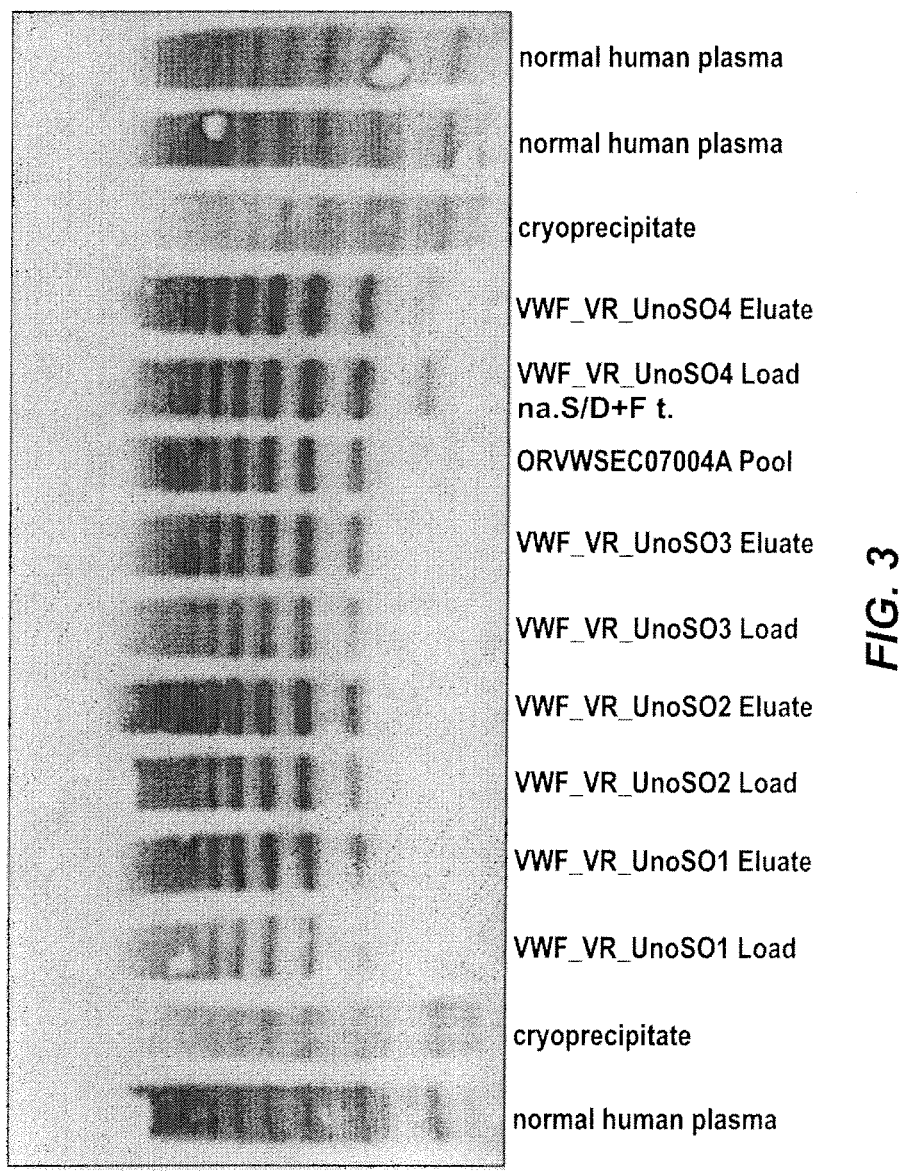
FIG. 3 shows the stained gel of the UNO S runs with MMV and REO virus spiked samples.
Figure 4:
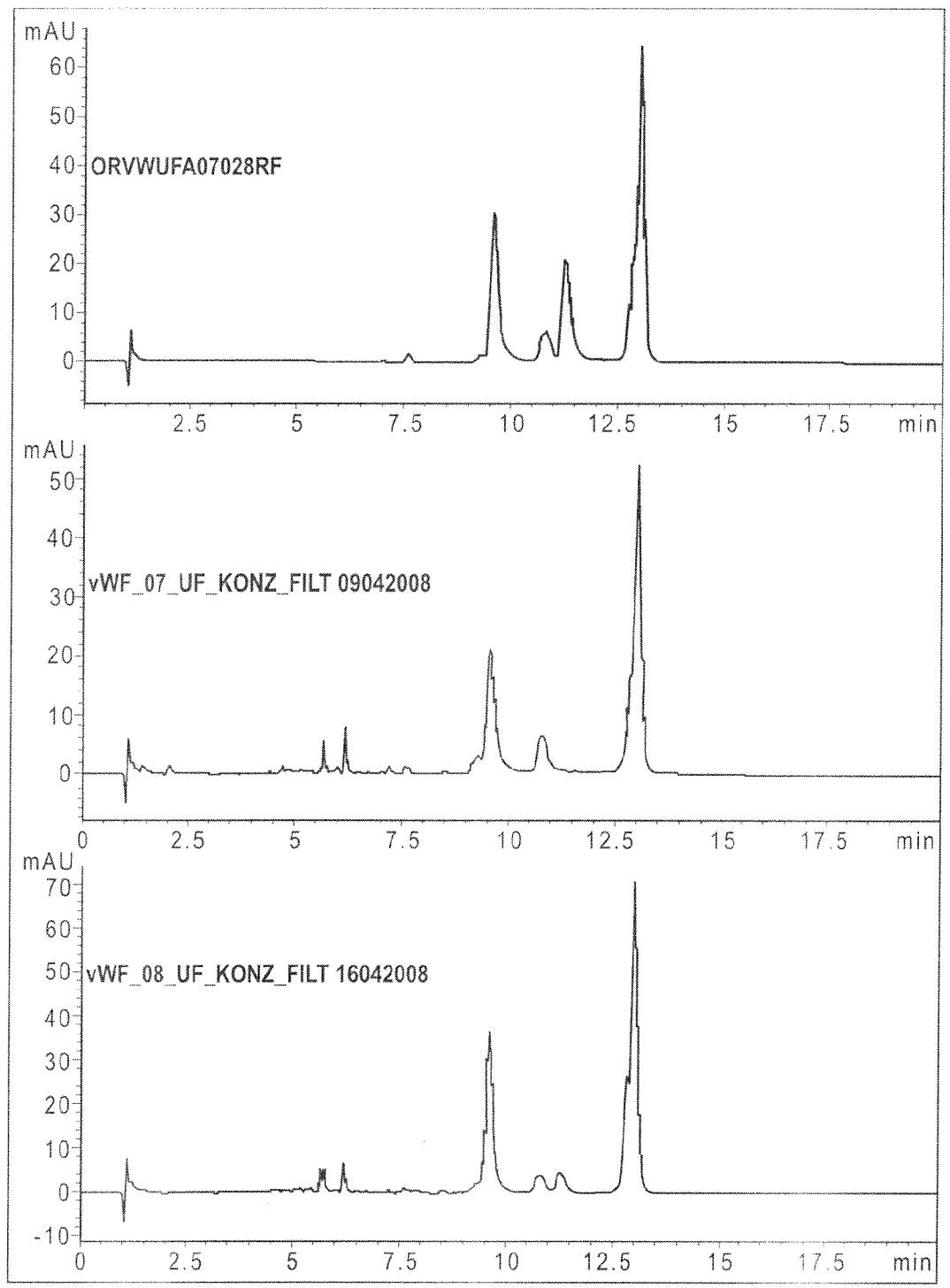
FIG. 4 shows the results of subjecting the purified preparations of rVWF obtained by the process variants to proteolytic digestion by V8 protease in the native state and separating the resulting peptides by RP-HPLC.
Figure 5:
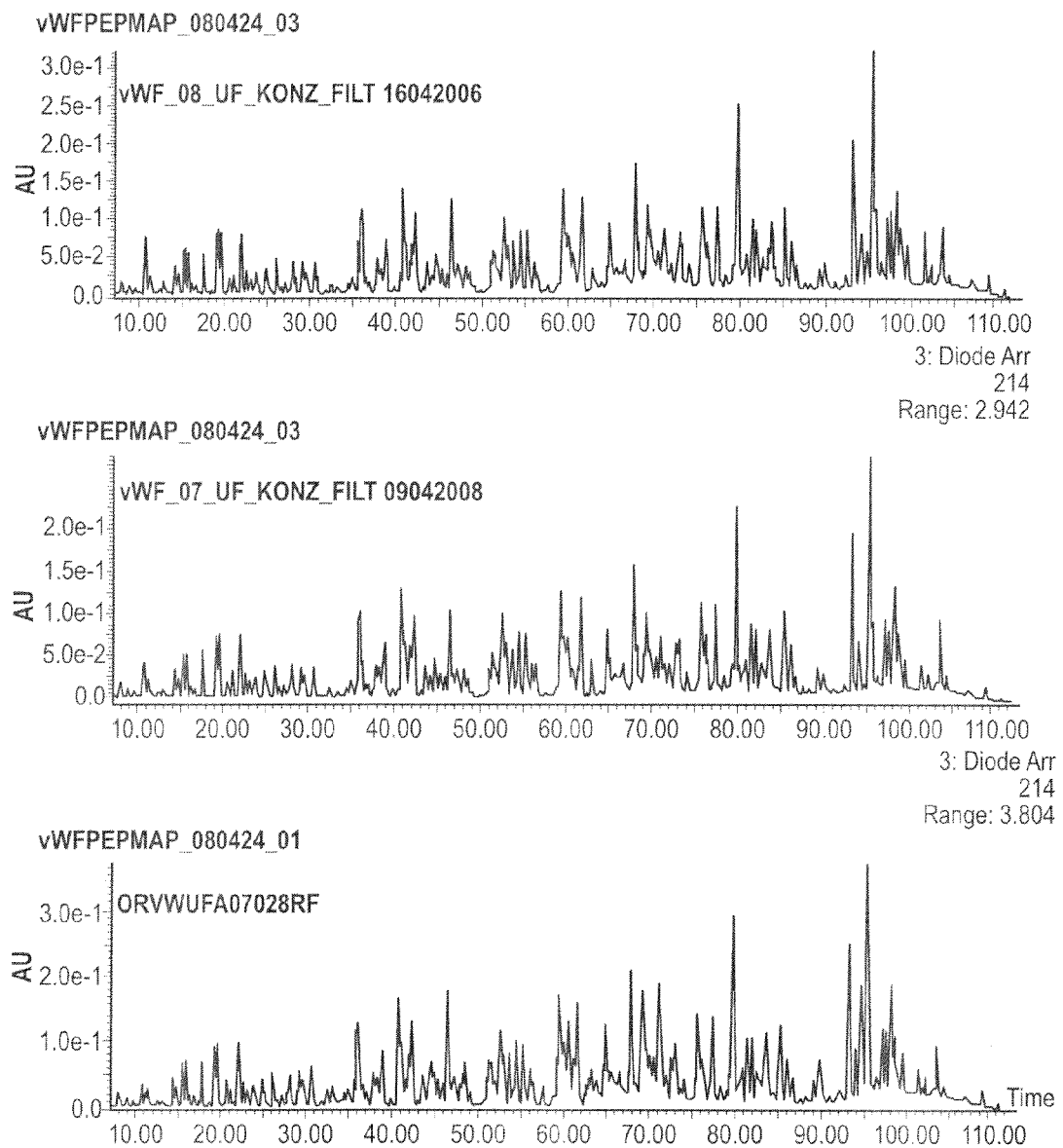
FIG. 5 shows the results of subjecting the purified preparations of rVWF obtained by the process variants to trypsin in the denatured state and separating the resulting peptides by RP-HPLC.

| Sample | UNO S #1 (pH 9 run) | UNO S #2 (Control run) | UNO S #3 (Control run pilot scale) |
|---|---|---|---|
| VWF RcoF Activity (U/ml) | 36.7 | 64.8 | 84.7 |
| VWF Antigen (µg/ml) | 715 | 1090 | 2010 |
| Specific activity (U/mg) | 51.3 | 59.4 | 42.1 |
| Collagen binding (U/ml) | 63.2 | 106.7 | 141.8 |
| Specific collagen binding activity (U/mg) | 88.4 | 97.9 | 70.5 |
| FVIII binding (%) | 51.7 | 64.6 | 63.1 |
| CHO protein (µg/ml) | 0.09 | 0.17 | n.d. |
| CHO DNA (pg/ml) | Non detectable | 10 | n.d. |
| Furin activity (mU/mi) | <6.25 | <6.25 | <6.25 |
| FVIII Ag (mUlml) | <125 | 152 | 1650 |
| FVIII Activity (mUlml) | 71 | 1452 | 6222 |
| Deamidation (mol %) | 5.1 | 3.7 | 5.0 |
| SDS-PAGE | | See FIG. 1 | |
| Multimer pattern (low resolution) | | See FIG. 2 | |
| Multimer pattern (high resolution) | | See FIG. 3 | |
| RP-HPLC | | See FIG. 4 | |
| Peptide Mapping | | See FIG. 5 | |

As can be seen from Table 2 the biochemical properties of rVWF purified by the different process variants are comparable.

The major band of the rVWF protein is very similar in all products whereas the extent of impurities is lower in sample #1 (denominated as VWF#07 in FIG. 1) by both silver staining and western blot analysis for residual rFVIII. The banding pattern for rFVIII is comparable between all batches which suggests that no degradation due to the pH 9.0 conditions occurred.

Low and high resolution agarose gel electrophoresis revealed the high similarity of the rVWF preparations. No differences in multimer composition by low resolution multimer analysis could be seen. FIG. 2 shows the stained gel of the UNO S runs with MMV and REO virus spiked samples. Also the high resolution multimer analysis revealed the intact multimer pattern suggesting no damage to the rVWF multimers occurred due to the pH 9.0 conditions. FIG. 3 shows the stained gel of the UNO S runs with MMV and REO virus spiked samples.

By the Isoquant assay no enhanced de-amidation could be detected due to the dwell time of rVWF at pH 9.0. Generally the molar percentage of deamidated rVWF is very low. Subjecting the purified preparations of rVWF obtained by the process variants to proteolytic digestion by either V8 protease in the native state (see FIG. 4) or trypsin (see FIG. 5) in the denatured state and separating the resulting peptides by RP-HPLC resulted in similar chromatograms for all samples.

Minor differences in the peak patterns are due to the presence of different amounts of impurities (mainly residual rVWF propeptide as can be seen in FIG. 1) in the preparations which was confirmed by mass spectrometry or N-terminal sequence analysis.

Example 3

Purification of rVWF by Cation Exchange Chromatography at High pH with MMV Spike A UNOsphere S resin packed into a column was activated with 1 CV of 2 M NaCl and equilibrated with 25 CV of an equilibration buffer (pH=9.0). Thereafter, a rVWF containing solution adjusted to a conductivity of 15 mS/cm and a pH of 9.0 and spiked with mouse minute virus (MMV) was loaded onto the column at a linear flow rate of about 10.0 cm/h. The column was then washed with 10 CV of equilibration buffer (pH=9.0) and the product was eluted with 3.5 CV of elution buffer (pH=7.5) at a linear flow rate of 65 cm/h. The increased pH during the loading and wash phase significantly reduced the binding of the virus particles to the resin but retained full binding of the product VWF. As a result, most of the loaded virus particles were found in the non-binding (flow through) and wash fraction separated from the product that was recovered in the eluate pool at high yields. The results in Table 3 show that by applying this procedure a virus removal capacity of 2 logs could be obtained with the non-enveloped model virus mouse minute virus (MMV).

The TCID50 assay was performed as follows. Briefly, serial ½ log dilutions of the samples were prepared in the appropriate tissue culture medium and 100 µl of each dilution were added to each of 8 wells of a microtiter plate seeded with the indicator cell tine. The cells were then incubated for 7 days at 36° C.±2° C. before the cytopathic effect was evaluated by visual inspection of the cells under a microscope. Median tissue culture infectious doses (TCID50) were calculated according to the Poisson distribution and expressed as $\log_{10}[TCID50/ml]$.

TABLE 3

Purification of rVWF on UNOsphere S

| | Volume ml | Virus titer (TCID50) $\log_{10}/ml$ | Virus content (TCID50) $\log_{10}$ | Reduction $\log_{10}$ |
|---|---|---|---|---|
| Load | 400 | 5.26 | 7.86 | — |
| Eluate pool | 89.4 | 3.8 | 5.75 | 2.11 |

The purification was performed using a column with 15 mm diameter and a bed height of 14 cm. Data shown are virus titers of active mouse minute virus.

Example 4

Purification of rVWF by Cation Exchange Chromatography at High pH with Reo Type 3 Virus Spike A UNOsphere S resin packed into a column was activated with 1 CV of 2 M NaCl and equilibrated with 25 CV of an equilibration buffer (pH=9.0). Thereafter, a rVWF containing solution adjusted to a conductivity of 15 mS/cm and a pH of 9.0 and spiked with various non-enveloped viruses was loaded onto the column at a linear flow rate of about 100 cm/h. The column was then washed with 10 CV of equilibration buffer (pH=9.0) and the product was eluted with 3.5 CV of elution buffer (pH=7.5) at a linear flow rate of 65 cm/h. The increased pH during the loading and wash phase significantly reduced the binding of the virus particles to the resin but retained full binding of the product VWF. As a result, most of the loaded virus particles were found in the non-binding (flow through) and wash fraction separated from the product that was recovered in the eluate pool at high yields. The results in Table 4 show that by applying this procedure a virus removal capacity of 2 logs could be obtained with the non-enveloped model virus mouse Reo Virus Type 3 (REO-III).

TABLE 4

Purification of rVWF on UNOsphere S

| | Volume ml | Virus titer (TCID50) $\log_{10}/ml$ | Virus content (TCID50) $\log_{10}$ | Reduction $\log_{10}$ |
|---|---|---|---|---|
| Load | 897 | 3.73 | 6.68 | — |
| Eluate pool | 89.3 | 2.61 | 4.56 | 2.12 |

The purification was performed using a column with 15 mm diameter and a bed height of 14 cm. Data shown are virus titers of active mouse Reovirus Type III (REO-III).

Example 5

Purification of rVWF on UNOsphere S According the Standard Procedure (Neutral pH)

A UNOsphere S resin packed into a column was activated with 1 CV of 2 M NaCl and equilibrated with 25 CV of an equilibration buffer (pH=6.5). Thereafter, a rVWF containing solution adjusted to a conductivity of 15 mS/cm and a pH of 6.5 and spiked with various non-enveloped viruses was loaded onto the column at a linear flow rate of about 100 cm/h. The column was then washed with 10 CV of equilibration buffer (pH=6.5) and the product was eluted with 3.5 CV of elution buffer (pH=7.5) at a linear flow rate of 65 cm/h. The virus titer of the various viruses tested were evaluated in the different chromatographic fractions (load, column flow through, wash, eluate, post eluate) and the reduction factors were calculated. The results in Table 5 show that by applying the standard purification procedure for VWF on UNOsphere S the removal capacity for non-enveloped viruses was insufficient for the different model viruses tested to claim a robust chromatographic step for removal of non-lipid enveloped viruses.

TABLE 5

VWF purification according to the standard procedure and the corresponding reduction capacities for non-enveloped viruses.

| | Reduction $\log_{10}$ | Comment Virus Characteristics |
|---|---|---|
| PPV (porcine Parvovirus) | <1 | small, DNA virus |
| hAdV (human Adenovirus) | 1.8 | large, DNA virus |
| EMCV (Enzephalo Myocarditis Virus) | <1 | small, RNA |
| Reo Virus Type III | 1.8 | large, RNA |
| MMV (mouse Minute Virus) | <1 | small, DNA |

The reduction rate is calculated as the total virus load in the load fraction divided by the total virus load in the eluate fraction expressed in logarithmic values.

What is claimed is:

1. A method for removing a non-lipid enveloped virus from a protein-containing solution comprising:
    applying the protein-containing solution to a cation exchange resin at a pH of 1.6 pH units or more above the isoelectric point of a protein in the protein-containing solution; and
    washing the cation exchange resin with a wash buffer to form an eluate, said wash buffer having a pH that is lower than the pH of the protein-containing solution applied to the cation exchange resin, wherein the protein has a molecular mass of at least about 150 kilodaltons, and whereby the non-lipid enveloped virus is removed from the protein-containing solution.

2. The method of claim 1, wherein the solution applied to the cation exchange resin is at least 1.8 pH units above the isoelectric point of VWF.

3. The method of claim 1, wherein the pH of the solution applied to the cation exchange resin is greater than 7.0.

4. The method of claim 1, wherein the cation exchange resin has a negatively charged group selected from the group consisting of carboxymethyl (CM), sulfoalkyl, sulfated esters of cellulose, heparin and methylsulfonate (S).

5. The method of claim 4, wherein the negatively charged sulfoalkyl group is sulfopropyl (SP) or sulfoethyl (SE).

6. The method of claim 1, wherein the pH of the wash buffer is greater than the isoelectric point of the VWF applied to the cation exchange resin.

7. A method for removing a non-lipid enveloped virus from a VWF-containing solution comprising:
    applying the solution to a cation exchange resin, wherein the pH of the solution is 2.0 pH units or more above the isoelectric point of VWF; and
    washing the cation exchange resin with a wash buffer to form an eluate, said wash buffer having a pH that is equal to or lower than the pH of the solution applied to the cation exchange resin, and whereby the non-lipid enveloped virus is removed from the VWF-containing solution.

8. The method of claim 7, wherein the pH of the VWF-containing solution and the wash buffer is about 9.0.

9. The method of claim 1, wherein the VWF-containing solution applied to the cation exchange resin is at least 2.0 pH units above the isoelectric point of the VWF.

* * * * *

SEQUENCE LISTING

<160> NUMBER OF SEQ ID NOS: 3

<210> SEQ ID NO 1
<211> LENGTH: 8833
<212> TYPE: DNA
<213> ORGANISM: Homo sapiens

<400> SEQUENCE: 1

```
agctcacagc tattgtggtg ggaaagggag ggtggttggt ggatgtcaca gcttgggctt      60
tatctccccc agcagtgggg actccacagc ccctgggcta cataacagca agacagtccg     120
gagctgtagc agacctgatt gagcctttgc agcagctgag agcatggcct agggtgggcg     180
gcaccattgt ccagcagctg agtttcccag ggaccttgga gatagccgca gccctcattt     240
gcagggaaag atgattcctg ccagatttgc cggggtgctg cttgctctgg ccctcatttt     300
gccagggacc ctttgtgcag aaggaactcg cggcaggtca tccacggccc gatgcagcct     360
tttcggaagt gacttcgtca acaccttga tgggagcatg tacagctttg cgggatactg     420
cagttacctc ctggcagggg gctgccagaa acgctccttc tcgattattg gggacttcca     480
gaatggcaag agagtgagcc tctccgtgta tcttggggaa ttttttgaca tccatttgtt     540
tgtcaatggt accgtgacac aggggaccca aagagtctcc atgccctatg cctccaaagg     600
gctgtatcta gaaactgagg ctgggtacta caagctgtcc ggtgaggcct atggctttgt     660
ggccaggatc gatggcagcg gcaactttca agtcctgctg tcagacagat acttcaacaa     720
gacctgcggg ctgtgtggca actttaacat ctttgctgaa gatgacttta tgacccaaga     780
agggaccttg acctcggacc cttatgactt tgccaactca tgggctctga gcagtggaga     840
acagtggtgt gaacgggcat ctcctcccag cagctcatgc aacatctcct ctggggaaat     900
gcagaagggc ctgtgggagc agtgccagct tctgaagagc acctcggtgt tgcccgctg     960
ccaccctctg gtggacccg agccttttgt ggccctgtgt gagaagactt tgtgtgagtg    1020
tgctgggggg ctggagtgcg cctgccctgc cctcctggag tacgcccgga cctgtgccca    1080
ggagggaatg gtgctgtacg gctggaccga ccacagcgcg tgcagcccag tgtgccctgc    1140
tggtatggag tataggcagt gtgtgtcccc ttgcgccagg acctgccaga gctgcacat    1200
caatgaaatg tgtcaggagc gatgcgtgga tggctgcagc tgccctgagg acagctcct    1260
ggatgaaggc ctctgcgtgg agagcaccga gtgtccctgc gtgcattccg gaaagcgcta    1320
ccctcccggc acctcctct ctcgagactg caacacctgc atttgccgaa acagccagtg    1380
gatctgcagc aatgaagaat gtccagggga gtgccttgtc acaggtcaat cacacttcaa    1440
gagctttgac aacagatact tcaccttcag tgggatctgc cagtacctgc tggcccggga    1500
ttgccaggac cactccttct ccattgtcat tgagactgtc cagtgtgctg atgaccgcga    1560
cgctgtgtgc acccgctccg tcaccgtccg gctgcctggc ctgcacaaca gccttgtgaa    1620
actgaagcat ggggcaggag ttgccatgga tggccaggac gtccagctcc ccctcctgaa    1680
aggtgacctc cgcatccagc atacagtgac ggcctccgtg cgcctcagct acggggagga    1740
cctgcagatg gactgggatg gccgcgggag gctgctggtg aagctgtccc ccgtctatgc    1800
cgggaagacc tgcggcctgt gtgggaatta caatggcaac cagggcgacg acttccttac    1860
cccctctggg ctggcggagc cccggtgga ggacttcggg aacgcctgga agctgcacgg    1920
ggactgccag gacctgcaga agcagcacag cgatccctgc gccctcaacc cgcgcatgac    1980
caggttctcc gaggaggcgt gcgcggtcct gacgtccccc acattcgagg cctgccatcg    2040
tgccgtcagc ccgctgccct acctgcggaa ctgccgctac gacgtgtgct cctgctcgga    2100
cggccgcgag tgcctgtgcg gcgccctggc cagctatgcc gcggcctgcg cggggagagg    2160
cgtgcgcgtc gcgtggcgcg agccaggccg ctgtgagctg aactgcccga aaggccaggt    2220
gtacctgcag tgcgggaccc cctgcaacct gacctgccgc tctctctctt acccggatga    2280
```

```
ggaatgcaat gaggcctgcc tggagggctg cttctgcccc ccagggctct acatggatga    2340
gaggggggac tgcgtgccca aggcccagtg cccctgttac tatgacggtg agatcttcca    2400
gccagaagac atcttctcag accatcacac catgtgctac tgtgaggatg cttcatgca    2460 ctgtaccatg agtggagtcc ccggaagctt gctgcctgac gctgtcctca gcagtccct    2520 gtctcatcgc agcaaaagga gcctatcctg tcggcccccc atggtcaagc tggtgtgtcc    2580
cgctgacaac ctgcgggctg aagggctcga gtgtaccaaa acgtgccaga actatgacct    2640
ggagtgcatg agcatgggct gtgtctctgg ctgcctctgc ccccgggca tggtccggca    2700 tgagaacaga tgtgtggccc tggaaaggtg tccctgcttc catcagggca aggagtatgc    2760
ccctggagaa acagtgaaga ttggctgcaa cacttgtgtc tgtcgggacc ggaagtggaa    2820
ctgcacagac catgtgtgtg atgccacgtg ctccacgatc ggcatggccc actacctcac    2880
cttcgacggg ctcaaatacc tgttccccgg ggagtgccag tacgttctgg tgcaggatta    2940
ctgcggcagt aaccctggga ccttcggat cctagtgggg aataagggat gcagccaccc    3000
ctcagtgaaa tgcaagaaac gggtcaccat cctggtggag gaggagaga ttgagctgtt    3060 tgacggggag gtgaatgtga agaggcccat gaaggatgag actcactttg aggtggtgga    3120
gtctggccgg tacatcattc tgctgctggg caaagccctc tccgtggtct gggaccgcca    3180
cctgagcatc tccgtggtcc tgaagcagac ataccaggag aaagtgtgtg gcctgtgtgg    3240
gaattttgat ggcatccaga acaatgacct caccagcagc aacctccaag tggaggaaga    3300
ccctgtggac tttgggaact cctggaaagt gagctcgcag tgtgctgaca ccagaaaagt    3360
gcctctggac tcatcccctg ccacctgcca taacaacatc atgaagcaga cgatggtgga    3420
ttcctcctgt agaatcctta ccagtgacgt cttccaggac tgcaacaagc tggtggaccc    3480
cgagccatat ctggatgtct gcatttacga cacctgctcc tgtgagtcca ttggggactg    3540
cgcctgcttc tgcgacacca ttgctgccta tgcccacgtg tgtgcccagc atggcaaggt    3600
ggtgacctgg aggacggcca cattgtgccc ccagagctgc gaggagagga atctccggga    3660
gaacgggtat gagtgtgagt ggcgctataa cagctgtgca cctgcctgtc aagtcacgtg    3720
tcagcaccct gagccactgg cctgcccgt gcagtgtgtg gagggctgcc atgcccactg    3780
ccctccaggg aaaatcctgg atgagctttt gcagacctgc gttgaccctg aagactgtcc    3840
agtgtgtgag gtggctggcc ggcgttttgc ctcaggaaag aaagtcacct tgaatcccag    3900
tgaccctgag cactgccaga tttgccactg tgatgttgtc aacctcacct gtgaagcctg    3960
ccaggagccg ggaggcctgg tggtgcctcc cacagatgcc ccggtgagcc ccaccactct    4020
gtatgtggag gacatctcgg aaccgccgtt gcacgatttc tactgcagca ggctactgga    4080
cctggtcttc ctgctggatg gctcctccag gctgtccgag gctgagtttg aagtgctgaa    4140
ggcctttgtg gtggacatga tggagcggct gcgcatctcc cagaagtggg tccgcgtggc    4200
cgtggtggag taccacgacg gctcccacgc ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc gccctgaagc    4380
ctcccgcatc accctgctcc tgatggccag ccaggagccc caacggatgt cccggaactt    4440
tgtccgctac gtccagggcc tgaagaagaa gaaggtcatt gtgatcccgg tgggcattgg    4500
gccccatgcc aacctcaagc agatccgcct catcgagaag caggcccctg agaacaaggc    4560
cttcgtgctg agcagtgtgg atgagctgga gcagcaaagg gacgagatcg ttagctacct    4620
ctgtgacctt gcccctgaag cccctcctcc tactctgccc cccgacatgg cacaagtcac    4680
```

```
tgtgggcccg gggctcttgg gggtttcgac cctggggccc aagaggaact ccatggttct    4740
ggatgtggcg ttcgtcctgg aaggatcgga caaaattggt gaagccgact caacaggag    4800
caaggagttc atggaggagg tgattcagcg gatggatgtg ggccaggaca gcatccacgt    4860
cacggtgctg cagtactcct acatggtgac tgtggagtac cccttcagcg aggcacagtc    4920
caaaggggac atcctgcagc gggtgcgaga gatccgctac cagggcggca acaggaccaa    4980
cactgggctg ccctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggccctaatg ccaacgtgca    5160
ggagctggag aggattggct ggcccaatgc ccctatcctc atccaggact tgagacgct    5220
cccccgagag gctcctgacc tggtgctgca gaggtgctgc tccggagagg ggctgcagat    5280
ccccaccctc tcccctgcac ctgactgcag ccagcccctg acgtgatcc ttctcctgga    5340
tggctcctcc agtttcccag cttcttattt tgatgaaatg aagagtttcg ccaaggcttt    5400
catttcaaaa gccaatatag ggcctcgtct cactcaggtg tcagtgctgc agtatggaag    5460
catcaccacc attgacgtgc catggaacgt ggtcccggag aaagcccatt tgctgagcct    5520
tgtggacgtc atgcagcggg agggaggccc cagccaaatc ggggatgcct gggctttgc    5580
tgtgcgatac ttgacttcag aaatgcatgg tgccaggccg ggagcctcaa aggcggtggt    5640
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggcccagcag gcgactccaa cgtggtgaag ctccagcgaa tcgaagacct    5820
ccctaccatg gtcaccttgg gcaattcctt cctccacaaa ctgtgctctg gatttgttag    5880
gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cggggctga ggccttcgtg ccctaacagc cagtcccctg ttaaagtgga    6060
agagacctgt ggctgccgct ggacctgccc ctgcgtgtgc acaggcagct ccactcggca    6120
catcgtgacc tttgatgggc agaatttcaa gctgactgga agctgttctt atgtcctatt    6180
tcaaaacaag gagcaggacc tggaggtgat tctccataat ggtgcctgca gccctggagc    6240
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catgaagtc aacgtttatg gtgccatcat gcatgaggtc agattcaatc accttggtca    6420
catcttcaca ttcactccac aaaacaatga gttccaactg cagctcagcc caagactttt    6480
tgcttcaaag acgtatggtc tgtgtgggat ctgtgatgag aacggagcca atgacttcat    6540
gctgagggat ggcacagtca ccacagactg gaaaacactt gttcaggaat ggactgtgca    6600
gcggccaggg cagacgtgcc agcccatcct ggaggagcag tgtcttgtcc ccgacagctc    6660
ccactgccag gtcctcctct taccactgtt tgctgaatgc cacaaggtcc tggctccagc    6720
cacattctat gccatctgcc agcaggacag ttgccaccag gagcaagtgt gtgaggtgat    6780
cgcctcttat gcccacctct gtcggaccaa cggggtctgc gttgactgga ggacacctga    6840
tttctgtgct atgtcatgcc caccatctct ggtctacaac cactgtgagc atggctgtcc    6900
ccggcactgt gatggcaacg tgagctcctg tggggaccat ccctccgaag gctgtttctg    6960
ccctccagat aaagtcatgt tggaaggcag ctgtgtccct gaagaggcct gcactcagtg    7020
```

-continued

```
cattggtgag gatggagtcc agcaccagtt cctggaagcc tgggtcccgg accaccagcc      7080
ctgtcagatc tgcacatgcc tcagcgggcg aaggtcaac tgcacaacgc agccctgccc       7140
cacggccaaa gctcccacgt gtggcctgtg tgaagtagcc cgcctccgcc agaatgcaga      7200
ccagtgctgc cccgagtatg agtgtgtgtg tgacccagtg agctgtgacc tgcccccagt      7260
gcctcactgt gaacgtggcc tccagcccac actgaccaac cctggcgagt gcagacccaa      7320
cttcacctgc gcctgcagga aggaggagtc aaaagagtg tccccaccct cctgcccccc       7380
gcaccgtttg cccacccttc ggaagaccca gtgctgtgat gagtatgagt gtgcctgcaa      7440
ctgtgtcaac tccacagtga gctgtcccct tgggtacttg gcctcaactg ccaccaatga      7500
ctgtggctgt accacaacca cctgccttcc cgacaaggtg tgtgtccacc gaagcaccat      7560
ctaccctgtg ggccagttct gggaggaggg ctgcgatgtg tgcacctgca ccgacatgga      7620
ggatgccgtg atgggcctcc gcgtggccca gtgctcccag aagccctgtg aggacagctg      7680
tcggtcgggc ttcacttacg ttctgcatga aggcgagtgc tgtggaaggt gcctgccatc      7740
tgcctgtgag gtggtgactg gctcaccgcg gggggactcc cagtcttcct ggaagagtgt      7800
cggctcccag tgggcctccc cggagaaccc ctgcctcatc aatgagtgtg tccgagtgaa      7860
ggaggaggtc tttatacaac aaaggaacgt ctcctgcccc cagctggagg tccctgtctg      7920
cccctcgggc tttcagctga gctgtaagac ctcagcgtgc tgcccaagct gtcgctgtga      7980
gcgcatggag gcctgcatgc tcaatggcac tgtcattggg cccgggaaga ctgtgatgat      8040
cgatgtgtgc acgacctgcc gctgcatggt gcaggtgggg gtcatctctg gattcaagct      8100
ggagtgcagg aagaccacct gcaaccctg cccctgggt tacaaggaag aaaataacac       8160
aggtgaatgt tgtgggagat gttttgcctac ggcttgcacc attcagctaa gaggaggaca      8220
gatcatgaca ctgaagcgtg atgagacgct ccaggatggc tgtgatactc acttctgcaa      8280
ggtcaatgag agaggagagt acttctggga gaagagggtc acaggctgcc caccctttga      8340
tgaacacaag tgtctggctg agggaggtaa aattatgaaa attccaggca cctgctgtga      8400
cacatgtgag gagcctgagt gcaacgacat cactgccagg ctgcagtatg tcaaggtggg      8460
aagctgtaag tctgaagtag aggtggatat ccactactgc cagggcaaat gtgccagcaa      8520
agccatgtac tccattgaca tcaacgatgt gcaggaccag tgctcctgct gctctccgac      8580
acggacggag cccatgcagg tggccctgca ctgcaccaat ggctctgttg tgtaccatga      8640
ggttctcaat gccatggagt gcaaatgctc ccccaggaag tgcagcaagt gaggctgctg      8700
cagctgcatg ggtgcctgct gctgcctgcc ttggcctgat ggccaggcca gagtgctgcc      8760
agtcctctgc atgttctgct cttgtgccct tctgagccca aataaaggc tgagctctta     8820
tcttgcaaaa ggc                                                         8833
```

<210> SEQ ID NO 2
<211> LENGTH: 2813
<212> TYPE: PRT
<213> ORGANISM: Homo sapiens

<400> SEQUENCE: 2

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45
```

```
Ser Met Tyr Ser Phe Ala Gly Tyr Cys Ser Tyr Leu Leu Ala Gly Gly
    50                  55                  60
Cys Gln Lys Arg Ser Phe Ser Ile Ile Gly Asp Phe Gln Asn Gly Lys
 65                  70                  75                  80
Arg Val Ser Leu Ser Val Tyr Leu Gly Glu Phe Phe Asp Ile His Leu
                 85                  90                  95
Phe Val Asn Gly Thr Val Thr Gln Gly Asp Gln Arg Val Ser Met Pro
            100                 105                 110
Tyr Ala Ser Lys Gly Leu Tyr Leu Glu Thr Glu Ala Gly Tyr Tyr Lys
            115                 120                 125
Leu Ser Gly Glu Ala Tyr Gly Phe Val Ala Arg Ile Asp Gly Ser Gly
130                 135                 140
Asn Phe Gln Val Leu Leu Ser Asp Arg Tyr Phe Asn Lys Thr Cys Gly
145                 150                 155                 160
Leu Cys Gly Asn Phe Asn Ile Phe Ala Glu Asp Asp Phe Met Thr Gln
                165                 170                 175
Glu Gly Thr Leu Thr Ser Asp Pro Tyr Asp Phe Ala Asn Ser Trp Ala
            180                 185                 190
Leu Ser Ser Gly Glu Gln Trp Cys Glu Arg Ala Ser Pro Pro Ser Ser
    195                 200                 205
Ser Cys Asn Ile Ser Ser Gly Glu Met Gln Lys Gly Leu Trp Glu Gln
210                 215                 220
Cys Gln Leu Leu Lys Ser Thr Ser Val Phe Ala Arg Cys His Pro Leu
225                 230                 235                 240
Val Asp Pro Glu Pro Phe Val Ala Leu Cys Glu Lys Thr Leu Cys Glu
                245                 250                 255
Cys Ala Gly Gly Leu Glu Cys Ala Cys Pro Ala Leu Leu Glu Tyr Ala
            260                 265                 270
Arg Thr Cys Ala Gln Glu Gly Met Val Leu Tyr Gly Trp Thr Asp His
            275                 280                 285
Ser Ala Cys Ser Pro Val Cys Pro Ala Gly Met Glu Tyr Arg Gln Cys
    290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
            340                 345                 350
Ser Gly Lys Arg Tyr Pro Pro Gly Thr Ser Leu Ser Arg Asp Cys Asn
            355                 360                 365
Thr Cys Ile Cys Arg Asn Ser Gln Trp Ile Cys Ser Asn Glu Glu Cys
    370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
            420                 425                 430
Ala Asp Asp Arg Asp Ala Val Cys Thr Arg Ser Val Thr Val Arg Leu
            435                 440                 445
Pro Gly Leu His Asn Ser Leu Val Lys Leu Lys His Gly Ala Gly Val
450                 455                 460
Ala Met Asp Gly Gln Asp Val Gln Leu Pro Leu Leu Lys Gly Asp Leu
```

-continued

```
            465                 470                 475                 480
        Arg Ile Gln His Thr Val Thr Ala Ser Val Arg Leu Ser Tyr Gly Glu
                            485                 490                 495
        Asp Leu Gln Met Asp Trp Asp Gly Arg Gly Arg Leu Leu Val Lys Leu
                        500                 505                 510
        Ser Pro Val Tyr Ala Gly Lys Thr Cys Gly Leu Cys Gly Asn Tyr Asn
                    515                 520                 525
        Gly Asn Gln Gly Asp Asp Phe Leu Thr Pro Ser Gly Leu Ala Glu Pro
                530                 535                 540
        Arg Val Glu Asp Phe Gly Asn Ala Trp Lys Leu His Gly Asp Cys Gln
        545                 550                 555                 560
        Asp Leu Gln Lys Gln His Ser Asp Pro Cys Ala Leu Asn Pro Arg Met
                            565                 570                 575
        Thr Arg Phe Ser Glu Glu Ala Cys Ala Val Leu Thr Ser Pro Thr Phe
                        580                 585                 590
        Glu Ala Cys His Arg Ala Val Ser Pro Leu Pro Tyr Leu Arg Asn Cys
                    595                 600                 605
        Arg Tyr Asp Val Cys Ser Cys Ser Asp Gly Arg Glu Cys Leu Cys Gly
                610                 615                 620
        Ala Leu Ala Ser Tyr Ala Ala Ala Cys Ala Gly Arg Gly Val Arg Val
        625                 630                 635                 640
        Ala Trp Arg Glu Pro Gly Arg Cys Glu Leu Asn Cys Pro Lys Gly Gln
                            645                 650                 655
        Val Tyr Leu Gln Cys Gly Thr Pro Cys Asn Leu Thr Cys Arg Ser Leu
                        660                 665                 670
        Ser Tyr Pro Asp Glu Glu Cys Asn Glu Ala Cys Leu Glu Gly Cys Phe
                    675                 680                 685
        Cys Pro Pro Gly Leu Tyr Met Asp Glu Arg Gly Asp Cys Val Pro Lys
                690                 695                 700
        Ala Gln Cys Pro Cys Tyr Tyr Asp Gly Glu Ile Phe Gln Pro Glu Asp
        705                 710                 715                 720
        Ile Phe Ser Asp His His Thr Met Cys Tyr Cys Glu Asp Gly Phe Met
                            725                 730                 735
        His Cys Thr Met Ser Gly Val Pro Gly Ser Leu Leu Pro Asp Ala Val
                        740                 745                 750
        Leu Ser Ser Pro Leu Ser His Arg Ser Lys Arg Ser Leu Ser Cys Arg
                    755                 760                 765
        Pro Pro Met Val Lys Leu Val Cys Pro Ala Asp Asn Leu Arg Ala Glu
                770                 775                 780
        Gly Leu Glu Cys Thr Lys Thr Cys Gln Asn Tyr Asp Leu Glu Cys Met
        785                 790                 795                 800
        Ser Met Gly Cys Val Ser Gly Cys Leu Cys Pro Pro Gly Met Val Arg
                            805                 810                 815
        His Glu Asn Arg Cys Val Ala Leu Glu Arg Cys Pro Cys Phe His Gln
                        820                 825                 830
        Gly Lys Glu Tyr Ala Pro Gly Glu Thr Val Lys Ile Gly Cys Asn Thr
                    835                 840                 845
        Cys Val Cys Arg Asp Arg Lys Trp Asn Cys Thr Asp His Val Cys Asp
                850                 855                 860
        Ala Thr Cys Ser Thr Ile Gly Met Ala His Tyr Leu Thr Phe Asp Gly
        865                 870                 875                 880
        Leu Lys Tyr Leu Phe Pro Gly Glu Cys Gln Tyr Val Leu Val Gln Asp
                            885                 890                 895
```

-continued

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

| Glu | Val | Leu | Lys | Ala | Phe | Val | Val | Asp | Met | Met | Glu | Arg | Leu | Arg |
|---|---|---|---|---|---|---|---|---|---|---|---|---|---|---|
| 1295 | | | | | 1300 | | | | | 1305 | | | | |

| Ile | Ser | Gln | Lys | Trp | Val | Arg | Val | Ala | Val | Val | Glu | Tyr | His | Asp |
|---|---|---|---|---|---|---|---|---|---|---|---|---|---|---|
| 1310 | | | | | 1315 | | | | | 1320 | | | | |

| Gly | Ser | His | Ala | Tyr | Ile | Gly | Leu | Lys | Asp | Arg | Lys | Arg | Pro | Ser |
|---|---|---|---|---|---|---|---|---|---|---|---|---|---|---|
| 1325 | | | | | 1330 | | | | | 1335 | | | | |

| Glu | Leu | Arg | Arg | Ile | Ala | Ser | Gln | Val | Lys | Tyr | Ala | Gly | Ser | Gln |
|---|---|---|---|---|---|---|---|---|---|---|---|---|---|---|
| 1340 | | | | | 1345 | | | | | 1350 | | | | |

| Val | Ala | Ser | Thr | Ser | Glu | Val | Leu | Lys | Tyr | Thr | Leu | Phe | Gln | Ile |
|---|---|---|---|---|---|---|---|---|---|---|---|---|---|---|
| 1355 | | | | | 1360 | | | | | 1365 | | | | |

| Phe | Ser | Lys | Ile | Asp | Arg | Pro | Glu | Ala | Ser | Arg | Ile | Thr | Leu | Leu |
|---|---|---|---|---|---|---|---|---|---|---|---|---|---|---|
| 1370 | | | | | 1375 | | | | | 1380 | | | | |

| Leu | Met | Ala | Ser | Gln | Glu | Pro | Gln | Arg | Met | Ser | Arg | Asn | Phe | Val |
|---|---|---|---|---|---|---|---|---|---|---|---|---|---|---|
| 1385 | | | | | 1390 | | | | | 1395 | | | | |

| Arg | Tyr | Val | Gln | Gly | Leu | Lys | Lys | Lys | Val | Ile | Val | Ile | Pro |
|---|---|---|---|---|---|---|---|---|---|---|---|---|---|
| 1400 | | | | | 1405 | | | | | 1410 | | | | |

| Val | Gly | Ile | Gly | Pro | His | Ala | Asn | Leu | Lys | Gln | Ile | Arg | Leu | Ile |
|---|---|---|---|---|---|---|---|---|---|---|---|---|---|---|
| 1415 | | | | | 1420 | | | | | 1425 | | | | |

| Glu | Lys | Gln | Ala | Pro | Glu | Asn | Lys | Ala | Phe | Val | Leu | Ser | Ser | Val |
|---|---|---|---|---|---|---|---|---|---|---|---|---|---|---|
| 1430 | | | | | 1435 | | | | | 1440 | | | | |

| Asp | Glu | Leu | Glu | Gln | Gln | Arg | Asp | Glu | Ile | Val | Ser | Tyr | Leu | Cys |
|---|---|---|---|---|---|---|---|---|---|---|---|---|---|---|
| 1445 | | | | | 1450 | | | | | 1455 | | | | |

| Asp | Leu | Ala | Pro | Glu | Ala | Pro | Pro | Pro | Thr | Leu | Pro | Pro | Asp | Met |
|---|---|---|---|---|---|---|---|---|---|---|---|---|---|---|
| 1460 | | | | | 1465 | | | | | 1470 | | | | |

| Ala | Gln | Val | Thr | Val | Gly | Pro | Gly | Leu | Leu | Gly | Val | Ser | Thr | Leu |
|---|---|---|---|---|---|---|---|---|---|---|---|---|---|---|
| 1475 | | | | | 1480 | | | | | 1485 | | | | |

| Gly | Pro | Lys | Arg | Asn | Ser | Met | Val | Leu | Asp | Val | Ala | Phe | Val | Leu |
|---|---|---|---|---|---|---|---|---|---|---|---|---|---|---|
| 1490 | | | | | 1495 | | | | | 1500 | | | | |

| Glu | Gly | Ser | Asp | Lys | Ile | Gly | Glu | Ala | Asp | Phe | Asn | Arg | Ser | Lys |
|---|---|---|---|---|---|---|---|---|---|---|---|---|---|---|
| 1505 | | | | | 1510 | | | | | 1515 | | | | |

| Glu | Phe | Met | Glu | Glu | Val | Ile | Gln | Arg | Met | Asp | Val | Gly | Gln | Asp |
|---|---|---|---|---|---|---|---|---|---|---|---|---|---|---|
| 1520 | | | | | 1525 | | | | | 1530 | | | | |

| Ser | Ile | His | Val | Thr | Val | Leu | Gln | Tyr | Ser | Tyr | Met | Val | Thr | Val |
|---|---|---|---|---|---|---|---|---|---|---|---|---|---|---|
| 1535 | | | | | 1540 | | | | | 1545 | | | | |

| Glu | Tyr | Pro | Phe | Ser | Glu | Ala | Gln | Ser | Lys | Gly | Asp | Ile | Leu | Gln |
|---|---|---|---|---|---|---|---|---|---|---|---|---|---|---|
| 1550 | | | | | 1555 | | | | | 1560 | | | | |

| Arg | Val | Arg | Glu | Ile | Arg | Tyr | Gln | Gly | Gly | Asn | Arg | Thr | Asn | Thr |
|---|---|---|---|---|---|---|---|---|---|---|---|---|---|---|
| 1565 | | | | | 1570 | | | | | 1575 | | | | |

| Gly | Leu | Ala | Leu | Arg | Tyr | Leu | Ser | Asp | His | Ser | Phe | Leu | Val | Ser |
|---|---|---|---|---|---|---|---|---|---|---|---|---|---|---|
| 1580 | | | | | 1585 | | | | | 1590 | | | | |

| Gln | Gly | Asp | Arg | Glu | Gln | Ala | Pro | Asn | Leu | Val | Tyr | Met | Val | Thr |
|---|---|---|---|---|---|---|---|---|---|---|---|---|---|---|
| 1595 | | | | | 1600 | | | | | 1605 | | | | |

| Gly | Asn | Pro | Ala | Ser | Asp | Glu | Ile | Lys | Arg | Leu | Pro | Gly | Asp | Ile |
|---|---|---|---|---|---|---|---|---|---|---|---|---|---|---|
| 1610 | | | | | 1615 | | | | | 1620 | | | | |

| Gln | Val | Val | Pro | Ile | Gly | Val | Gly | Pro | Asn | Ala | Asn | Val | Gln | Glu |
|---|---|---|---|---|---|---|---|---|---|---|---|---|---|---|
| 1625 | | | | | 1630 | | | | | 1635 | | | | |

| Leu | Glu | Arg | Ile | Gly | Trp | Pro | Asn | Ala | Pro | Ile | Leu | Ile | Gln | Asp |
|---|---|---|---|---|---|---|---|---|---|---|---|---|---|---|
| 1640 | | | | | 1645 | | | | | 1650 | | | | |

| Phe | Glu | Thr | Leu | Pro | Arg | Glu | Ala | Pro | Asp | Leu | Val | Leu | Gln | Arg |
|---|---|---|---|---|---|---|---|---|---|---|---|---|---|---|
| 1655 | | | | | 1660 | | | | | 1665 | | | | |

| Cys | Cys | Ser | Gly | Glu | Gly | Leu | Gln | Ile | Pro | Thr | Leu | Ser | Pro | Ala |
|---|---|---|---|---|---|---|---|---|---|---|---|---|---|---|
| 1670 | | | | | 1675 | | | | | 1680 | | | | |

| Pro | Asp | Cys | Ser | Gln | Pro | Leu | Asp | Val | Ile | Leu | Leu | Leu | Asp | Gly |
|---|---|---|---|---|---|---|---|---|---|---|---|---|---|---|

```
            1685                1690                1695

Ser Ser Ser Phe Pro Ala Ser Tyr Phe Asp Glu Met Lys Ser Phe
    1700                1705                1710

Ala Lys Ala Phe Ile Ser Lys Ala Asn Ile Gly Pro Arg Leu Thr
    1715                1720                1725

Gln Val Ser Val Leu Gln Tyr Gly Ser Ile Thr Thr Ile Asp Val
    1730                1735                1740

Pro Trp Asn Val Val Pro Glu Lys Ala His Leu Leu Ser Leu Val
    1745                1750                1755

Asp Val Met Gln Arg Glu Gly Gly Pro Ser Gln Ile Gly Asp Ala
    1760                1765                1770

Leu Gly Phe Ala Val Arg Tyr Leu Thr Ser Glu Met His Gly Ala
    1775                1780                1785

Arg Pro Gly Ala Ser Lys Ala Val Val Ile Leu Val Thr Asp Val
    1790                1795                1800

Ser Val Asp Ser Val Asp Ala Ala Ala Asp Ala Ala Arg Ser Asn
    1805                1810                1815

Arg Val Thr Val Phe Pro Ile Gly Ile Gly Asp Arg Tyr Asp Ala
    1820                1825                1830

Ala Gln Leu Arg Ile Leu Ala Gly Pro Ala Gly Asp Ser Asn Val
    1835                1840                1845

Val Lys Leu Gln Arg Ile Glu Asp Leu Pro Thr Met Val Thr Leu
    1850                1855                1860

Gly Asn Ser Phe Leu His Lys Leu Cys Ser Gly Phe Val Arg Ile
    1865                1870                1875

Cys Met Asp Glu Asp Gly Asn Glu Lys Arg Pro Gly Asp Val Trp
    1880                1885                1890

Thr Leu Pro Asp Gln Cys His Thr Val Thr Cys Gln Pro Asp Gly
    1895                1900                1905

Gln Thr Leu Leu Lys Ser His Arg Val Asn Cys Asp Arg Gly Leu
    1910                1915                1920

Arg Pro Ser Cys Pro Asn Ser Gln Ser Pro Val Lys Val Glu Glu
    1925                1930                1935

Thr Cys Gly Cys Arg Trp Thr Cys Pro Cys Val Cys Thr Gly Ser
    1940                1945                1950

Ser Thr Arg His Ile Val Thr Phe Asp Gly Gln Asn Phe Lys Leu
    1955                1960                1965

Thr Gly Ser Cys Ser Tyr Val Leu Phe Gln Asn Lys Glu Gln Asp
    1970                1975                1980

Leu Glu Val Ile Leu His Asn Gly Ala Cys Ser Pro Gly Ala Arg
    1985                1990                1995

Gln Gly Cys Met Lys Ser Ile Glu Val Lys His Ser Ala Leu Ser
    2000                2005                2010

Val Glu Leu His Ser Asp Met Glu Val Thr Val Asn Gly Arg Leu
    2015                2020                2025

Val Ser Val Pro Tyr Val Gly Gly Asn Met Glu Val Asn Val Tyr
    2030                2035                2040

Gly Ala Ile Met His Glu Val Arg Phe Asn His Leu Gly His Ile
    2045                2050                2055

Phe Thr Phe Thr Pro Gln Asn Asn Glu Phe Gln Leu Gln Leu Ser
    2060                2065                2070

Pro Lys Thr Phe Ala Ser Lys Thr Tyr Gly Leu Cys Gly Ile Cys
    2075                2080                2085
```

```
Asp Glu Asn Gly Ala Asn Asp Phe Met Leu Arg Asp Gly Thr Val
    2090                2095                2100

Thr Thr Asp Trp Lys Thr Leu Val Gln Glu Trp Thr Val Gln Arg
    2105                2110                2115

Pro Gly Gln Thr Cys Gln Pro Ile Leu Glu Glu Gln Cys Leu Val
    2120                2125                2130

Pro Asp Ser Ser His Cys Gln Val Leu Leu Pro Leu Phe Ala
    2135                2140                2145

Glu Cys His Lys Val Leu Ala Pro Ala Thr Phe Tyr Ala Ile Cys
    2150                2155                2160

Gln Gln Asp Ser Cys His Gln Glu Gln Val Cys Glu Val Ile Ala
    2165                2170                2175

Ser Tyr Ala His Leu Cys Arg Thr Asn Gly Val Cys Val Asp Trp
    2180                2185                2190

Arg Thr Pro Asp Phe Cys Ala Met Ser Cys Pro Pro Ser Leu Val
    2195                2200                2205

Tyr Asn His Cys Glu His Gly Cys Pro Arg His Cys Asp Gly Asn
    2210                2215                2220

Val Ser Ser Cys Gly Asp His Pro Ser Glu Gly Cys Phe Cys Pro
    2225                2230                2235

Pro Asp Lys Val Met Leu Glu Gly Ser Cys Val Pro Glu Glu Ala
    2240                2245                2250

Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
    2270                2275                2280

Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475
```

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 3
<211> LENGTH: 2050
<212> TYPE: PRT
<213> ORGANISM: Homo sapiens

<400> SEQUENCE: 3

Ser Leu Ser Cys Arg Pro Pro Met Val Lys Leu Val Cys Pro Ala Asp
1               5                   10                  15

-continued

```
Asn Leu Arg Ala Glu Gly Leu Glu Cys Thr Lys Thr Cys Gln Asn Tyr
             20                  25                  30

Asp Leu Glu Cys Met Ser Met Gly Cys Val Ser Gly Cys Leu Cys Pro
         35                  40                  45

Pro Gly Met Val Arg His Glu Asn Arg Cys Val Ala Leu Glu Arg Cys
 50                  55                  60

Pro Cys Phe His Gln Gly Lys Glu Tyr Ala Pro Gly Glu Thr Val Lys
 65                  70                  75                  80

Ile Gly Cys Asn Thr Cys Val Cys Arg Asp Arg Lys Trp Asn Cys Thr
                 85                  90                  95

Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
             115                 120                 125

Val Leu Val Gln Asp Tyr Cys Gly Ser Asn Pro Gly Thr Phe Arg Ile
 130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                 165                 170                 175

Glu Val Asn Val Lys Arg Pro Met Lys Asp Glu Thr His Phe Glu Val
             180                 185                 190

Val Glu Ser Gly Arg Tyr Ile Ile Leu Leu Leu Gly Lys Ala Leu Ser
             195                 200                 205

Val Val Trp Asp Arg His Leu Ser Ile Ser Val Val Leu Lys Gln Thr
         210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
             245                 250                 255

Asp Phe Gly Asn Ser Trp Lys Val Ser Ser Gln Cys Ala Asp Thr Arg
             260                 265                 270

Lys Val Pro Leu Asp Ser Ser Pro Ala Thr Cys His Asn Asn Ile Met
             275                 280                 285

Lys Gln Thr Met Val Asp Ser Ser Cys Arg Ile Leu Thr Ser Asp Val
         290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                 325                 330                 335

Phe Cys Asp Thr Ile Ala Ala Tyr Ala His Val Cys Ala Gln His Gly
             340                 345                 350

Lys Val Val Thr Trp Arg Thr Ala Thr Leu Cys Pro Gln Ser Cys Glu
         355                 360                 365

Glu Arg Asn Leu Arg Glu Asn Gly Tyr Glu Cys Glu Trp Arg Tyr Asn
 370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
             405                 410                 415

Gly Lys Ile Leu Asp Glu Leu Leu Gln Thr Cys Val Asp Pro Glu Asp
             420                 425                 430
```

```
Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Thr Leu Leu Leu Met Ala Ser
    610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
        675                 680                 685

Glu Ile Val Ser Tyr Leu Cys Asp Leu Ala Pro Glu Ala Pro Pro Pro
    690                 695                 700

Thr Leu Pro Pro Asp Met Ala Gln Val Thr Val Gly Pro Gly Leu Leu
705                 710                 715                 720

Gly Val Ser Thr Leu Gly Pro Lys Arg Asn Ser Met Val Leu Asp Val
                725                 730                 735

Ala Phe Val Leu Glu Gly Ser Asp Lys Ile Gly Glu Ala Asp Phe Asn
            740                 745                 750

Arg Ser Lys Glu Phe Met Glu Glu Val Ile Gln Arg Met Asp Val Gly
        755                 760                 765

Gln Asp Ser Ile His Val Thr Val Leu Gln Tyr Ser Tyr Met Val Thr
    770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
            820                 825                 830

Asp Arg Glu Gln Ala Pro Asn Leu Val Tyr Met Val Thr Gly Asn Pro
        835                 840                 845

Ala Ser Asp Glu Ile Lys Arg Leu Pro Gly Asp Ile Gln Val Val Pro
```

-continued

```
                850                 855                 860
Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu Gly Leu
                900                 905                 910

Gln Ile Pro Thr Leu Ser Pro Ala Pro Asp Cys Ser Gln Pro Leu Asp
            915                 920                 925

Val Ile Leu Leu Leu Asp Gly Ser Ser Ser Phe Pro Ala Ser Tyr Phe
            930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
                965                 970                 975

Thr Ile Asp Val Pro Trp Asn Val Val Pro Glu Lys Ala His Leu Leu
            980                 985                 990

Ser Leu Val Asp Val Met Gln Arg  Glu Gly Gly Pro Ser  Gln Ile Gly
        995                 1000                 1005

Asp Ala  Leu Gly Phe Ala Val  Arg Tyr Leu Thr Ser  Glu Met His
    1010                 1015                 1020

Gly Ala  Arg Pro Gly Ala Ser  Lys Ala Val Val Ile  Leu Val Thr
    1025                 1030                 1035

Asp Val  Ser Val Asp Ser Val  Asp Ala Ala Ala Asp  Ala Ala Arg
    1040                 1045                 1050

Ser Asn  Arg Val Thr Val Phe  Pro Ile Gly Ile Gly  Asp Arg Tyr
    1055                 1060                 1065

Asp Ala  Ala Gln Leu Arg Ile  Leu Ala Gly Pro Ala  Gly Asp Ser
    1070                 1075                 1080

Asn Val  Val Lys Leu Gln Arg  Ile Glu Asp Leu Pro  Thr Met Val
    1085                 1090                 1095

Thr Leu  Gly Asn Ser Phe Leu  His Lys Leu Cys Ser  Gly Phe Val
    1100                 1105                 1110

Arg Ile  Cys Met Asp Glu Asp  Gly Asn Glu Lys Arg  Pro Gly Asp
    1115                 1120                 1125

Val Trp  Thr Leu Pro Asp Gln  Cys His Thr Val Thr  Cys Gln Pro
    1130                 1135                 1140

Asp Gly  Gln Thr Leu Leu Lys  Ser His Arg Val Asn  Cys Asp Arg
    1145                 1150                 1155

Gly Leu  Arg Pro Ser Cys Pro  Asn Ser Gln Ser Pro  Val Lys Val
    1160                 1165                 1170

Glu Glu  Thr Cys Gly Cys Arg  Trp Thr Cys Pro Cys  Val Cys Thr
    1175                 1180                 1185

Gly Ser  Ser Thr Arg His Ile  Val Thr Phe Asp Gly  Gln Asn Phe
    1190                 1195                 1200

Lys Leu  Thr Gly Ser Cys Ser  Tyr Val Leu Phe Gln  Asn Lys Glu
    1205                 1210                 1215

Gln Asp  Leu Glu Val Ile Leu  His Asn Gly Ala Cys  Ser Pro Gly
    1220                 1225                 1230

Ala Arg  Gln Gly Cys Met Lys  Ser Ile Glu Val Lys  His Ser Ala
    1235                 1240                 1245

Leu Ser  Val Glu Leu His Ser  Asp Met Glu Val Thr  Val Asn Gly
    1250                 1255                 1260
```

```
Arg Leu Val Ser Val Pro Tyr Val Gly Gly Asn Met Glu Val Asn
    1265            1270            1275

Val Tyr Gly Ala Ile Met His Glu Val Arg Phe Asn His Leu Gly
    1280            1285            1290

His Ile Phe Thr Phe Thr Pro Gln Asn Asn Glu Phe Gln Leu Gln
    1295            1300            1305

Leu Ser Pro Lys Thr Phe Ala Ser Lys Thr Tyr Gly Leu Cys Gly
    1310            1315            1320

Ile Cys Asp Glu Asn Gly Ala Asn Asp Phe Met Leu Arg Asp Gly
    1325            1330            1335

Thr Val Thr Thr Asp Trp Lys Thr Leu Val Gln Glu Trp Thr Val
    1340            1345            1350

Gln Arg Pro Gly Gln Thr Cys Gln Pro Ile Leu Glu Glu Gln Cys
    1355            1360            1365

Leu Val Pro Asp Ser Ser His Cys Gln Val Leu Leu Leu Pro Leu
    1370            1375            1380

Phe Ala Glu Cys His Lys Val Leu Ala Pro Ala Thr Phe Tyr Ala
    1385            1390            1395

Ile Cys Gln Gln Asp Ser Cys His Gln Glu Gln Val Cys Glu Val
    1400            1405            1410

Ile Ala Ser Tyr Ala His Leu Cys Arg Thr Asn Gly Val Cys Val
    1415            1420            1425

Asp Trp Arg Thr Pro Asp Phe Cys Ala Met Ser Cys Pro Pro Ser
    1430            1435            1440

Leu Val Tyr Asn His Cys Glu His Gly Cys Pro Arg His Cys Asp
    1445            1450            1455

Gly Asn Val Ser Ser Cys Gly Asp His Pro Ser Glu Gly Cys Phe
    1460            1465            1470

Cys Pro Pro Asp Lys Val Met Leu Glu Gly Ser Cys Val Pro Glu
    1475            1480            1485

Glu Ala Cys Thr Gln Cys Ile Gly Glu Asp Gly Val Gln His Gln
    1490            1495            1500

Phe Leu Glu Ala Trp Val Pro Asp His Gln Pro Cys Gln Ile Cys
    1505            1510            1515

Thr Cys Leu Ser Gly Arg Lys Val Asn Cys Thr Thr Gln Pro Cys
    1520            1525            1530

Pro Thr Ala Lys Ala Pro Thr Cys Gly Leu Cys Glu Val Ala Arg
    1535            1540            1545

Leu Arg Gln Asn Ala Asp Gln Cys Cys Pro Glu Tyr Glu Cys Val
    1550            1555            1560

Cys Asp Pro Val Ser Cys Asp Leu Pro Pro Val Pro His Cys Glu
    1565            1570            1575

Arg Gly Leu Gln Pro Thr Leu Thr Asn Pro Gly Glu Cys Arg Pro
    1580            1585            1590

Asn Phe Thr Cys Ala Cys Arg Lys Glu Glu Cys Lys Arg Val Ser
    1595            1600            1605

Pro Pro Ser Cys Pro Pro His Arg Leu Pro Thr Leu Arg Lys Thr
    1610            1615            1620

Gln Cys Cys Asp Glu Tyr Glu Cys Ala Cys Asn Cys Val Asn Ser
    1625            1630            1635

Thr Val Ser Cys Pro Leu Gly Tyr Leu Ala Ser Thr Ala Thr Asn
    1640            1645            1650
```

-continued

```
Asp Cys Gly Cys Thr Thr Thr Thr Cys Leu Pro Asp Lys Val Cys
1655                1660                1665

Val His Arg Ser Thr Ile Tyr Pro Val Gly Gln Phe Trp Glu Glu
    1670                1675                1680

Gly Cys Asp Val Cys Thr Cys Thr Asp Met Glu Asp Ala Val Met
    1685                1690                1695

Gly Leu Arg Val Ala Gln Cys Ser Gln Lys Pro Cys Glu Asp Ser
1700                1705                1710

Cys Arg Ser Gly Phe Thr Tyr Val Leu His Glu Gly Glu Cys Cys
    1715                1720                1725

Gly Arg Cys Leu Pro Ser Ala Cys Glu Val Val Thr Gly Ser Pro
1730                1735                1740

Arg Gly Asp Ser Gln Ser Ser Trp Lys Ser Val Gly Ser Gln Trp
    1745                1750                1755

Ala Ser Pro Glu Asn Pro Cys Leu Ile Asn Glu Cys Val Arg Val
1760                1765                1770

Lys Glu Glu Val Phe Ile Gln Gln Arg Asn Val Ser Cys Pro Gln
    1775                1780                1785

Leu Glu Val Pro Val Cys Pro Ser Gly Phe Gln Leu Ser Cys Lys
1790                1795                1800

Thr Ser Ala Cys Cys Pro Ser Cys Arg Cys Glu Arg Met Glu Ala
    1805                1810                1815

Cys Met Leu Asn Gly Thr Val Ile Gly Pro Gly Lys Thr Val Met
1820                1825                1830

Ile Asp Val Cys Thr Thr Cys Arg Cys Met Val Gln Val Gly Val
    1835                1840                1845

Ile Ser Gly Phe Lys Leu Glu Cys Arg Lys Thr Thr Cys Asn Pro
1850                1855                1860

Cys Pro Leu Gly Tyr Lys Glu Glu Asn Asn Thr Gly Glu Cys Cys
    1865                1870                1875

Gly Arg Cys Leu Pro Thr Ala Cys Thr Ile Gln Leu Arg Gly Gly
1880                1885                1890

Gln Ile Met Thr Leu Lys Arg Asp Glu Thr Leu Gln Asp Gly Cys
    1895                1900                1905

Asp Thr His Phe Cys Lys Val Asn Glu Arg Gly Glu Tyr Phe Trp
1910                1915                1920

Glu Lys Arg Val Thr Gly Cys Pro Pro Phe Asp Glu His Lys Cys
    1925                1930                1935

Leu Ala Glu Gly Gly Lys Ile Met Lys Ile Pro Gly Thr Cys Cys
1940                1945                1950

Asp Thr Cys Glu Glu Pro Glu Cys Asn Asp Ile Thr Ala Arg Leu
    1955                1960                1965

Gln Tyr Val Lys Val Gly Ser Cys Lys Ser Glu Val Glu Val Asp
1970                1975                1980

Ile His Tyr Cys Gln Gly Lys Cys Ala Ser Lys Ala Met Tyr Ser
    1985                1990                1995

Ile Asp Ile Asn Asp Val Gln Asp Gln Cys Ser Cys Cys Ser Pro
2000                2005                2010

Thr Arg Thr Glu Pro Met Gln Val Ala Leu His Cys Thr Asn Gly
    2015                2020                2025
```

-continued

```
Ser Val Val Tyr His Glu Val Leu Asn Ala Met Glu Cys Lys Cys
    2030            2035                2040

Ser Pro Arg Lys Cys Ser Lys
    2045            2050
```